US009170156B2

(12) United States Patent
Li et al.

(10) Patent No.: US 9,170,156 B2
(45) Date of Patent: Oct. 27, 2015

(54) NORMAL-INCIDENCE BROADBAND SPECTROSCOPIC POLARIMETER CONTAINING REFERENCE BEAM AND OPTICAL MEASUREMENT SYSTEM

(75) Inventors: Guoguang Li, Beijing (CN); Tao Liu, Beijing (CN); Jiangyan Zhao, Beijing (CN); Qingyang Guo, Beijing (CN); Edgar Genio, Beijing (CN); Tiezhong Ma, Beijing (CN); Yang Xia, Beijing (CN)

(73) Assignee: Bei Optics Technology Co., Ltd., Beijing (CN)

( * ) Notice: Subject to any disclaimer, the term of this patent is extended or adjusted under 35 U.S.C. 154(b) by 0 days.

(21) Appl. No.: 14/366,637

(22) PCT Filed: Sep. 6, 2012

(86) PCT No.: PCT/CN2012/081071
§ 371 (c)(1),
(2), (4) Date: Jun. 18, 2014

(87) PCT Pub. No.: WO2013/091404
PCT Pub. Date: Jun. 27, 2013

(65) Prior Publication Data
US 2014/0354991 A1    Dec. 4, 2014

(30) Foreign Application Priority Data
Dec. 19, 2011    (CN) .......................... 2011 1 0427910

(51) Int. Cl.
*G01J 4/00*    (2006.01)
*G01J 3/447*    (2006.01)
(Continued)

(52) U.S. Cl.
CPC ................ *G01J 3/447* (2013.01); *G01B 11/02* (2013.01); *G01J 3/0208* (2013.01); *G01J 3/0224* (2013.01);
(Continued)

(58) Field of Classification Search
CPC ........... G01J 3/447; G01J 4/04; G01J 3/0224; G01J 3/021; G01J 3/0208; G10J 4/00; G01N 2021/213; G01N 2021/214; G01N 21/211; G01N 21/21; G01B 11/0641; G01B 2210/56
See application file for complete search history.

(56) References Cited

U.S. PATENT DOCUMENTS 5,747,813 A    5/1998    Norton
7,233,401 B1    6/2007    Houser

FOREIGN PATENT DOCUMENTS

CN    101799326 A    8/2010
CN    101802543 A    8/2010
(Continued)

OTHER PUBLICATIONS

International Search Report (Form PCT/ISA/210) for PCT/CN2012/081071, completed Dec. 6, 2012.

*Primary Examiner* — Kara E Geisel
*Assistant Examiner* — Rufus Phillips
(74) *Attorney, Agent, or Firm* — Koppel, Patrick, Heybl & Philpott

(57) ABSTRACT

Disclosed is a normal-incidence broadband spectroscopic polarimeter containing reference beam, comprising a light source, a first reflecting unit, a first concentrating unit, a second concentrating unit, a polarizer, a first curved mirror, a first planar mirror, a second reflecting unit and a probing unit. Also disclosed is an optical measurement system, comprising the normal-incidence broadband spectroscopic polarimeter containing reference beam. The normal-incidence broadband spectroscopic polarimeter containing reference beam achieves an integral combination of the light beams after splitting, can maintain the polarization state of the light beams while increasing the light transmission efficiency, and has a low complexity.

25 Claims, 12 Drawing Sheets

(51) Int. Cl.
  *G02B 27/14* (2006.01)
  *G02B 27/40* (2006.01)
  *G01J 3/42* (2006.01)
  *G01J 3/02* (2006.01)
  *G01B 11/02* (2006.01)
  *G01N 21/21* (2006.01)

(52) U.S. Cl.
  CPC . *G01J 3/42* (2013.01); *G02B 27/14* (2013.01); *G02B 27/40* (2013.01); *G01B 2210/56* (2013.01); *G01N 21/21* (2013.01); *G01N 2021/213* (2013.01)

(56) References Cited

FOREIGN PATENT DOCUMENTS

| | | |
|---|---|---|
| CN | 102269623 A | 12/2011 |
| WO | WO 2011/045967 A1 | 4/2011 |

--Prior Art--

NORMAL-INCIDENCE BROADBAND SPECTROSCOPIC POLARIMETER CONTAINING REFERENCE BEAM AND OPTICAL MEASUREMENT SYSTEM

TECHNICAL FIELD OF THE INVENTION

The disclosure relates to the field of optics, and in particular to a normal-incidence broadband spectroscopic polarimeter containing reference beam and an optical measurement system.

BACKGROUND OF THE INVENTION

Generally, a key step in optical measurement technique is to make the probing beam focused onto the sample. Two methods are currently widely used. One method is to separate the last focusing lens from other components and only to adjust the focusing lens to focus the probing beam onto the sample. For example, as shown in FIG. 1, the focusing is achieved by moving the last focusing lens up and down. The other method is to adjust the whole optical measurement system to focus the probing beam on the sample. For example, as shown in FIG. 2, the focusing is achieved by moving the whole optical system up and down (for example, refer to the U.S. Pat. No. 5,747,813 and U.S. Pat. No. 5,486,701).

With the rapid development of semiconductor industry, it becomes very critical to apply optical technology to accurately measure the Critical Dimension (CD), spatial profile and material characteristics of three-dimensional structures formed by the single-layer film or multilayer film on wafers. While detecting the wafers with normal sizes of 150 mm, 200 mm or 300 mm, its surface may not be flat due to various reasons such as film stress. Therefore, when the whole wafer is detected, auto-focusing for each measurement point is a key technique to achieve high accuracy and rapid measurement and ensure production of semiconductor production line. And it is widely known that focusing the broadband probing beam into a small size spot on the sample surface is highly desired. The small size spot allows to measure the micro-structured patterns and broadband probing beam is helpful for better measurement accuracy. There are some issues in the first focusing method in this case: lens usually has chromatic aberration which results in different wavelengths of light focusing on different locations, increasing the error and thus reducing the measurement accuracy. It is also hard to find the lens materials with good transmission in the whole broadband wavelength range. Those skilled in the art can clearly understand that the entire optical system is adjusted by the second focusing method, and it is very difficult to achieve precise measurement due to the requirements and limits on the weight and speed of the system.

For these reasons, a new method was proposed by those skilled in the art, that is, focusing the broadband probing beam on the sample surface by using the curved mirror (for example, refer to U.S. Pat. No. 5,608,526 and U.S. Pat. No. 7,505,133B1, U.S. Patent Application Publication No. 2007/0247624A1 and Chinese Patent Application Publication No. 101467306A). This method has advantages as below: the mirror does not produce chromatic aberration in whole wavelength range, and has high reflectivity in wide wavelength range.

Although the application of curved mirror does not produce chromatic aberration and thus improve the focusing and measurement accuracy, compared with lens, it is more difficult to align the optical path with curved mirror. The adjustment of focus point and spatial orientation of curved mirror was constrained by incident light, often requiring the simultaneous adjustment of the entire optical system for better adjustment and control of the output optical path and focus point. For example, (1) elliptical mirror: While the spatial location of two focus points is relatively fixed, the adjustable range of optical path and focusing position is very limited by adjusting the individual elliptical mirror after the incident light path was corrected. (2) Toroidal mirror: Although the two corresponding focus points can be achieved in a certain range of incident angles, the spatial relationship of the two focus points changes with the relationship between incident light and toroidal mirror, and the correlations between two focus points are complex and it is very difficult to achieve focusing. Another drawback is that its adjustable range is small and is easy to create image aberrations. (3) Off-axis parabolic mirror: The adjustable range is very limited because the aberrations were resulted as the angle of off-axis parabolic mirror change relative to the direction of incident light. While a wide range of the focusing position can be achieved by moving the off-axis parabolic mirror along the direction of the collimated light beam, the relative position of focus point to the off-axis parabolic mirror centre cannot be changed. This also limits the adjustable range of the focus points. In summary, the use of a single curved mirror itself does not produce chromatic aberration, but it is difficult to adjust and control the direction of the optical path and focusing positions by simple adjustment. Furthermore, the polarization state of beam will be changed after reflected by a single mirror. Here, taking an aluminium mirror as an example, the reflectivities Rs and Rp of S and P polarized light at two incident angles are as shown in FIG. 3a. The above two curves represent the reflectivity Rs of S polarized light. The below two curves represent the reflectivity Rp of P polarized light. The solid line corresponds to an incident angle of 45 degrees, and the dotted line corresponds to an incident angle of 50 degrees. As a result, the reflectivities of S and P polarized light are not equal, and changed with the incident angle. The phase difference between the S and P polarized light reflected is as shown in FIG. 3b. The solid line corresponds to an incident angle of 45 degrees, and the dotted line corresponds to an incident angle of 50 degrees. As a result, the phase difference between the S and P polarized light is different, changed with the incident angle, and associated with the wavelength. In short, because the polarization states S and P with the polarization direction orthogonal to each other have different reflectivity and phase change, after broadband beam being reflected by a mirror, the polarization states of broadband beam varies, resulting in the control of the change of beam polarization difficult (for example, refer to U.S. Pat. No. 6,829,049B1 and U.S. Pat. No. 6,667,805).

The polarization control capability of the spectrometer defines the scope of its applications. Take Optical Critical Dimension (OCD) equipment as an example. Such equipment is widely used in integrated circuit manufacturing lines for process controls. The OCD equipment can measure the Critical Dimension (CD), three-dimensional profile of periodic pattern on sample surface, film thickness and optical constants of multilayer materials by measuring reflectance spectra and phase characteristics of the polarized beam from the sample surface and fitting numerical simulation results. For the spectrometer achieving the critical dimension measurement, the focusing system of spectrometer must be able to control the polarization state of the beam in the process of focusing and optical signal collection in order to measure the sample accurately.

Furthermore, two methods are often used for optical measurement of semiconductor film, i.e., absolute reflectivity measurement method and elliptical polarization measurement method. As described in Chinese Patent Applications No. 201110032744.8, when the absolute reflectivity measurement method is used for measurement, a standard sample is needed to measure, and the measurement result of the standard sample is recorded as a reference value. Then, a sample to be tested is measured, and the measurement result of the sample to be tested is compared to the reference value from the measured standard sample to obtain a relatively true value of the sample to be tested. Due to the light source itself, the spectral intensity thereof may be changed (drifted) during the actual measurement. Theoretically, generally assume that the spectral intensity of the light source is exactly the same when the standard sample and the sample to be tested are measured. But actually, since the sample to be tested and the standard sample cannot be measured at the same time, the changed of the spectral intensity of the light source will influence the measurement result.

For these reasons, it is proposed by those skilled in the art that the reference beam is used for calibrating the light source fluctuation. That is, the light emitted from the light source is divided into two beams. One is used as a probing beam to record the optical information of the sample. The other is used as a reference beam. By measuring the reference beam, the spectral intensity of the light source can be recorded respectively when the reference sample and the sample to be tested are measured, to correct the change of the spectral intensity of the light source during measurement and improve the measurement accuracy.

The measurement equipment is often classified into an optical system with normal-incidence relative to the sample surface and an optical system with oblique incidence relative to the sample surface. The optical system with normal-incidence, due to more compact structure, is often integrated with other process equipment to achieve the integration of production and measurement and real-time monitoring. In the prior art, the normal-incidence spectrometer calibrated by reference beam is achieved by two methods as follows:

(1) As shown in FIG. 4, divergent light emitted from the light source 101 is incident on a beam splitter 103 parallelly after passing through the lens 102. The light transmitted by the beam splitter 103 is used as a probing beam, and the light reflected by the beam splitter 103 is used as a reference beam. The probing beam is focused on the surface of the sample 105 after being converged by the lens 104. The reflected light on the surface of the sample 105 is reflected by the lens 104, thereafter, incident on the beam splitter 103 perpendicularly. The probing beam reflected by the beam splitter 103 is converged by the lens 107 and incident on a probe 108 to obtain the reflection spectrum on the sample surface. The reference beam is incident on a planar mirror 106 perpendicularly, and incident on the beam splitter 103 perpendicularly after being reflected by the planar mirror 106. The reference beam is also converged by the lens 107 after being transmitted by the beam splitter 103, and incident on the probe 108 to obtain the reference spectrum containing light source spectral characteristics (for example, refer to U.S. Pat. No. 7,067,818B2, U.S. Pat. No. 7,189,973B2 and U.S. Pat. No. 7,271,394B2, and U.S. Patent Application Publication No. 2005/0002037A1). In this spectrometer, a controlling aperture can be used for selecting the beam needed to be measured. The method has the advantages as follows: the light source fluctuation can be calibrated, but due to the use of the beam splitter, the spectrometer also has the following problems: (i) light transmission is low. The beam must be transmitted and reflected once by the same beam splitter via the light source during the whole measurement to enter the probe. Assume that the beam splitter has 50% of transmittivity and 50% of reflectivity. The maximum light transmission ratio that the probing beam and the reference beam can reach is only 25%. (ii) If the high quality spot and wide spectral range are achieved simultaneously, it is necessary to deal with chromatic dispersion. The complexity and cost of the system are high. (2) A planar mirror is inserted in the optical path, to make a part of light emitted from the light source is incident on the planar mirror, and the other part pass through the edge of the planar mirror. The beam reflected by the planar mirror is incident on the sample surface perpendicularly as probing beam. The beam passing through the edge of the planar mirror is used as reference beam. The probing beam and the reference beam enter two different spectrometers respectively for simultaneous measurement (for example, refer to U.S. Pat. No. 5,747,813 and U.S. Pat. No. 6,374,967B1). The method has the following advantages: the simultaneous measurement of probing beam and reference beam during measurement corrects the spectrum and intensity changes of the light source accurately; the loss of light intensity during measurement is small and the utilization ratio is high. However, due to the use of two different spectrometers, the photoelectric conversion efficiency is not the same, and the wavelength distribution and resolution are also not the same. Therefore, it is not easy to calibrate the system, and the measurement accuracy will be reduced. On the other hand, the optical path has complex structure in the scheme, and cannot be adjusted easily. The two spectrometers increase the volume of the equipment and increase the cost.

When the spectrometer without polarizer was used to measure the sample with periodic structures, as described in Chinese Patent Applications No. 201010270454.2, the incident beam must be natural light because the rotation angle of incident beam cannot be adjusted relative to the anisotropic angle of samples. In theory, the natural light emitted from light source is required to arrive on the sample surface by either maintaining absolutely polarization or passing through none of polarization-sensitive components. The anisotropic samples cannot be measured if polarization states were presently partly; under this circumstance, the measured values change as the anisotropic samples rotate. Therefore, the spectrometer capable of measuring the anisotropic samples while without polarization control demands the high quality of optical elements and the sophisticated adjustment of the optical path. During measurement, the light reflected by the sample is partially polarized. When the beam is incident on the probe, in theory, the polarization of the incident beam either was maintained completely or no polarization-sensitive component was present in the path. For example, if a polarization-sensitive component was encountered in the path, a depolarizer is required, thus it will reduce the signal to noise ratio. Moreover, the above problem cannot be corrected by numerical methods.

SUMMARY OF THE INVENTION

The technical problem solved by the invention is to provide a normal-incidence broadband spectroscopic polarimeter containing reference beam, which has the following features: the focus is easily adjusted, no chromatic aberration is introduced, the polarization characteristics are maintained, the light transmission efficiency is high and it is easy to achieve, and an optical measurement system.

According to one aspect of the invention, there is provided a normal-incidence broadband spectroscopic polarimeter containing reference beam, comprising: a light source, a first reflecting unit, a first concentrating unit, a second concentrating unit, a polarizer, a first curved mirror, a first planar mirror, a second reflecting unit and a probing unit, wherein the first reflecting unit is used for splitting light emitted from the light source into a probing beam and a reference beam, and making the probing beam incident on the first concentrating unit, and making the reference beam incident on the second concentrating unit;

the first concentrating unit is used for receiving the probing beam, and making the beam incident on the polarizer after becoming a parallel beam;

the polarizer is provided between the first concentrating unit and the first curved mirror, and used for making the parallel beam pass there through and incident on the first curved mirror;

the first curved mirror is used for receiving the parallel beam passing through the polarizer and making the beam be a focused beam;

the first planar mirror is used for receiving the focused beam and reflecting the focused beam to focus on a sample perpendicularly;

the second concentrating unit is used for receiving the reference beam, and making the reference beam incident on the second reflecting unit;

the second reflecting unit is used for receiving the probing beam reflected by the sample and passing through the planar mirror, the first curved mirror, the polarizer, and the first concentrating unit in order and the reference beam passing through the second concentrating unit respectively or simultaneously, and making the received beams incident on the probing unit; and the probing unit is used for probing the beam reflected by the second reflecting unit.

According to another aspect of the invention, there is provided an optical measurement system, comprising the normal-incidence broadband spectroscopic polarimeter.

The normal-incidence broadband spectroscopic polarimeter containing reference beam provided by the invention achieves an integral combination of the light beams after splitting, can maintain the polarization state of the light beams while increasing the light transmission efficiency, and has a lower complexity than the prior art.

DETAILED DESCRIPTION OF THE EMBODIMENTS

As stated above, in the prior art, although the use of curved mirror itself does not produce chromatic aberration, it is difficult to adjust and to control the direction of the optical path and the focusing position by simple adjustment. In view of these problems, a method of adjusting the focus by using a planar mirror is proposed by the invention.

Figure 5:
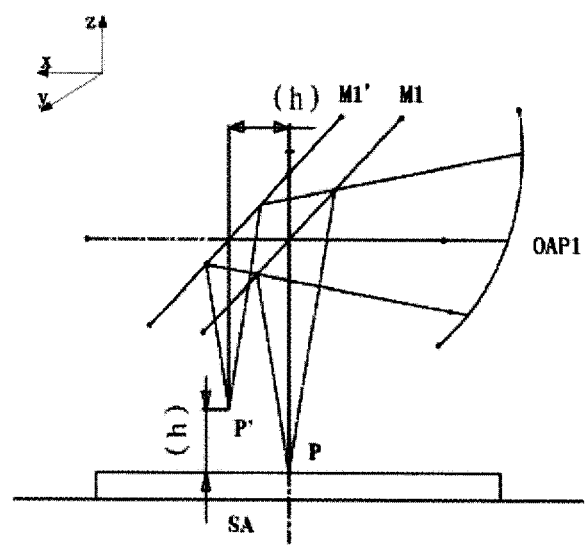
FIG. 5 is a schematic drawing for describing the realization of the focus by moving the planar mirror.
Figure 6A:
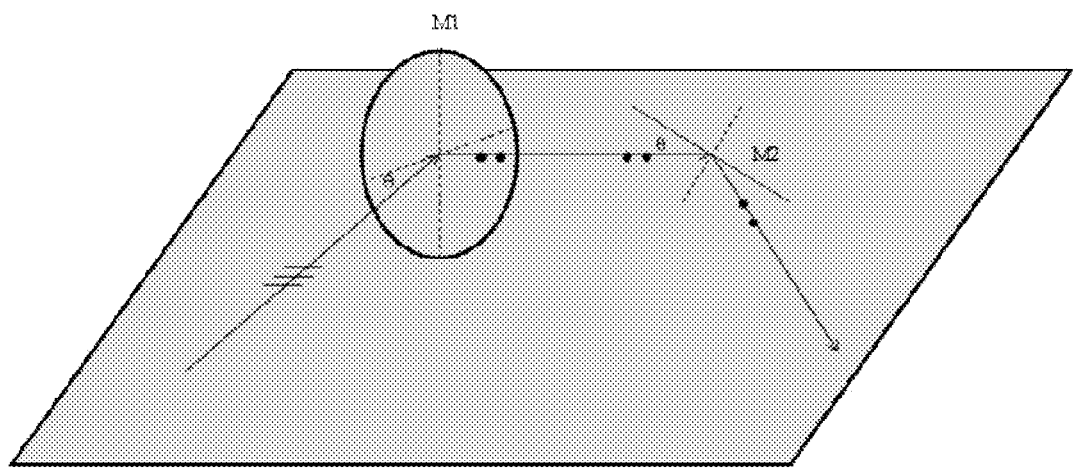
FIG. 6a-6c are schematic drawings for explaining the maintaining of polarization characteristics of a polarized light.
Figure 6B:
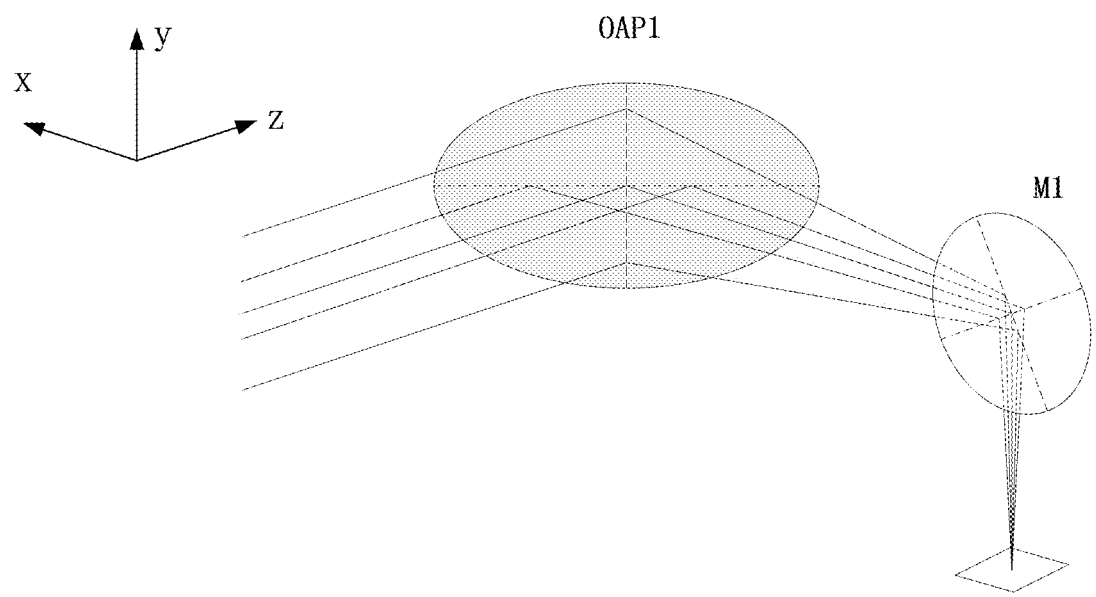
Figure 6C:
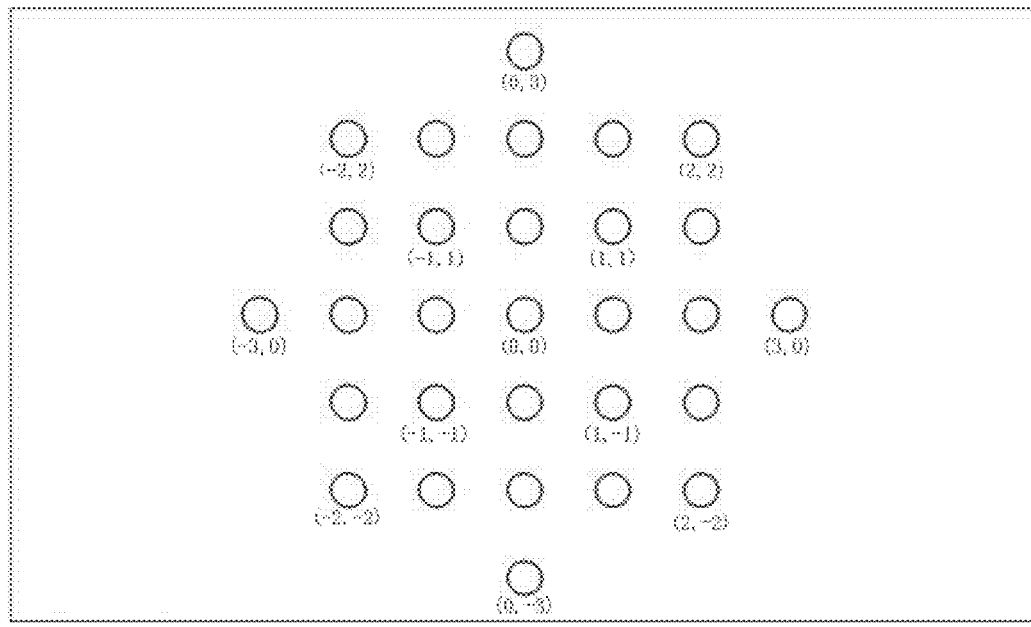

The principles of focusing of the invention are described in conjunction with FIG. 5, and the principles of maintaining the polarization characteristics of any polarized light are described in conjunction with FIG. 6a to FIG. 6c.

As shown in FIG. 5, assuming that: the focused beam from off-axis parabolic mirror OAP1 is focused on the position P of sample SA after being reflected by planar mirror M1, the main light in the focused beam propagates along the horizontal direction and is incident on the planar mirror M1 at an incident angle of 45 degrees. When the planar mirror M1 moves a distance h along the propagation direction of the main light of the focused beam (i.e., planar mirror is moved to the position M1'), the position P' of the focused beam from off-axis parabolic mirror OAP1 after being reflected by planar mirror M1' relative to the original focus position P moves a distance h in a vertical direction, and also moves a distance h in the propagation direction of the main light. If the focus point on the samples needs to move upward by distance h, one only needs to move the planar mirror M1 further also by the distance h relative to the off-axis parabolic mirror OAP1, while moving the sample platform by the same distance along the moving direction of the planar mirror M1. As a result, those skilled in the art can easily adjust the focus position of the light beam to adapt to the change of the sample height.

Moreover, since the planar mirror itself does not affect the focus condition of incident light and does not produce chromatic aberration, the use of mirror can maintain the focused beam quality while changing the beam propagation direction. In addition, on one hand, the planar mirror is often used in folding optical path to make the whole optical system more compact. On the other hand, the planar mirror can realize high reflectivity in broadband spectral range and have little influence on the light intensity; and integrate with the aid of the focus judgment method, the planar mirrors can realize the accurate manual or automatic focusing. Therefore, in present invention, the focus was realized by adjusting the planar mirror.

With reference to FIG. 6a and FIG. 6b, the basic principles of maintaining polarization characteristics of polarized light through two planar mirrors or one planar mirror and one off-axis parabolic mirror can be explained as below.

As shown in FIG. 6a, assume that the S (or P) polarized beam with the incident plane of the first planar mirror M1 as reference enters the first planar mirror M1 at the incident angle of (90-θ) and is reflected to the second planar mirror M2 by the first planar mirror M1. When the incident plane of the first planar mirror M1 is perpendicular to the incident plane of the second planar mirror M2, and the second planar mirror M2 is tilted to meet the beam reflected by the first planar mirror M1 incident on the second planar mirror M2 at the incident angle of (90-θ), the S (or P) polarized light with the incident plane of the first planar mirror M1 as reference will change into P (or S) polarized light with the incident plane on the second planar mirror M2 as reference after being reflected by the first planar mirror M1.

Now analyze the changes of the propagation direction and the polarization state of the beam with the right-handed reference system established by taking the beam propagation direction as +Z direction. The above process can be expressed by a mathematical formula below:

$$\begin{cases} Ex = E_{1s} \\ Ey = E_{1p} \end{cases} \quad (a)$$

The polarization components E1s, E1p with the incident plane of the first planar mirror M1 as the reference are defined as +X and +Y direction component in the right-handed reference system, respectively. After being reflected by M1, $$\begin{cases} E'_{1s} = r_{1s}E_{1s} \\ E'_{1p} = r_{1p}E_{1p} \end{cases} \quad (b)$$

$E_{1s}'$, $E_{1p}'$ represent the polarization components of reflected light with the incident plane of the first planar mirror M1 as reference respectively; $r_{1s}$ and $r_{1p}$ respectively represent the reflectivity of S- and P-polarized lights incident on the first planar mirror M1 with incident plane of the first planar mirror M1 as reference at an incident angle of (90-θ). And, $$\begin{cases} E_{2s} = E'_{1p} \\ E_{2p} = -E'_{1s} \end{cases} \quad (c)$$

After reflected by the first planar mirror M1, the $E_{1s}'$, $E_{1p}'$ become the incident lights of M2 with the polarization components $-E_{2p}$ and $E_{2s}$, respectively, with the incident plane of the second planar mirror M2 as reference. After reflected by the second planar mirror M2, $$\begin{cases} E'_{2s} = r_{2s}E_{2s} \\ E'_{2p} = r_{2p}E_{2p} \end{cases} \quad (d)$$

$E_{2s}'$, $E_{2p}'$ represent the polarization components of reflected light with the incident plane of the second planar mirror M2 as reference, $r_{2s}$ and $r_{2p}$ represent the reflectivity on the second mirror M2 of the S-polarization and P-polarization components respectively, which enter M2 at an angle of (90-θ) and take incident plane of M2 as reference.

Due to the right-hand rule, the polarization direction of S-polarized light which takes incident plane of the first planar mirror M1 as reference is the negative direction of the P-polarized light which takes incident plane of the second planar mirror M2 as reference. Set the polarization component of S-polarized beam which takes incident plane of the first planar mirror M1 as reference is always along the positive direction of X-axis in the right-handed reference system which is established by taking the beam propagation direction as +Z direction. After the beam is reflected by the second planar mirror M2, the polarization direction of P-polarized beam, with incident plane of the second planar mirror M2 as reference, is in the positive direction of X-axis; so, the polarization direction of S-polarized beam, with incident plane of the second planar mirror M2 as reference, is in the negative direction of Y-axis. Thus:

$$\begin{cases} E'_{2p} = E'_x \\ E'_{2s} = -E'_y \end{cases} \quad (e)$$

$E_x'$, $E_y'$ represent the polarization components of emergent light. When the first planar mirror M1 and the second planar mirror M2 have the same reflective materials and the same coating structure:

$$\begin{cases} r_{1s} = r_{2s} \\ r_{1p} = r_{2p} \end{cases} \quad (f)$$

Based on the above formulae, there is:

$$\begin{cases} \dfrac{E_x}{E_y} = \dfrac{E'_x}{E'_y} \end{cases} \quad (g)$$

In the above formulae (a)-(g), all the variables are complex. The formula (g) shows that the polarization component ratio of emergent light equals to that of the incident light. Therefore, with the above two planar mirrors, the polarization characteristics of polarized light can be maintained.

According to the above formulae (a)-(e), it is known as long as the first planar mirror M1 and the second planar mirror M2 satisfy the relation of $r_{2s}r_{1p}=r_{2p}r_{1s}$, the relationship in formula (g) can be obtained. That is, if two mirrors satisfy the relation of $r_{2s}r_{1p}=r_{2p}r_{1s}$, then through the two mirrors, polarization characteristics of polarized light can be maintained.

It can be seen that, in the system consisting of two planar mirrors with the incident plane perpendicular to each other and with the same incident angle, the polarization characteristics of the incident light can be perfectly maintained. With an assumption that one of the above two planar mirrors was replaced with an off-axis parabolic mirror which has the same reflective material and the same coating structure, the two mirror system was simulated for the case of small numerical aperture (NA). Although the polarization characteristics of the beam will have deviations after passing the system constituted by the off-axis parabolic mirror and planar mirror, when the parallel beam is focused with a small NA, the deviations of the polarization characteristics are not sufficient to affect the accuracy of measurement. For the strict polarization requirement, the measurement results can be further calibrated using numerical calculations.

For example, take FIG. 6b as an example, a parallel beam is a circularly polarized light before being incident onto the off-axis parabolic mirror OAP1, i.e., Ex=Ey, and Phase(Ex)−Phase(Ey)=90 degrees, where Ex and Ey are the amplitudes of the electric vector of the beam in the x and y directions respectively, and Phase(Ex) and Phase(Ey) are the phases of the electric vector of the beam in the x and y directions respectively. After focused by off-axis parabolic mirror, the cone half angle of focused beam is 4.2 degrees (NA=0.073). When the wavelength of incident light is 210 nm, the calculated point distribution within the cross section of incident light is shown in FIG. 6c (29 points in total and already partially marked, for example, (0, 3) to (0, 0)). After numerical calculation, the intensity changes and phase changes of polarization in the focus point are listed in Table 1. Polarization intensity variation is defined as |Ex/Ey|−1, and the phase variation is defined as Phase(Ex)−Phase(Ey)−90. It can be seen from the table that, because the intensity changes and phase changes of the polarized beam with a central symmetry of (0, 0) are quite closely complementary, the above changes as a whole can further alleviate influence caused by error.

structure and meet the conditions that incident angles of the main light are the same and the incident planes of the main light are perpendicular to each other (within the allowed error range, that is, including the situation that incident angles are approximately the same and incident planes are nearly perpendicular to each other), the polarization characteristics of arbitrary polarized light will remain unchanged after reflected by the two mirrors. The example of mirrors with the same reflective material and the same coating structure are the mirrors simultaneously coated in the same vacuum chamber.

In addition, if the two mirrors do not have the same reflective material and the same coating structure and only meet the conditions of the beam incident planes perpendicular or parallel to each other, only when the probing beam is linearly polarized and the polarization direction is perpendicular or parallel to the incident plane, the polarization state can be remained unchanged.

As described below, in the broadband spectrometer of the present invention, there are two methods to achieve focus.

The first method is to observe the changes of signal intensity of collected reflected light to achieve focus. Compared to the focused state, defocus state will result in the loss of peripheral part of the light spot in the optical collection system after the location of spectrometer slit is calibrated. After rough focusing process, the most accurate focus can be obtained by finding the maximum intensity of optical signal. The mathematical methods and basic steps of quickly finding the focus point are as follows: in the vicinity of focus point, the relationship between the optical signal intensity and defocus distance is approximated by a quadratic curve type, i.e., the parabola: $I=-A(x-x_0)^2+B$, where I is optical signal intensity, $x_0$ is focus position, A and B are the coefficients. As

TABLE 1

| Coordinates of incident plane | Intensity changes of polarization | Phase changes of polarization (degree) | Coordinates of incident plane | Intensity changes of polarization | Phase changes of polarization (degree) |
|---|---|---|---|---|---|
| (−3, 0) | 0.0011 | 2.1107 | (3, 0) | −0.0069 | −2.6477 |
| (−2, −2) | 0.0205 | 2.3577 | (2, 2) | −0.0244 | −2.1827 |
| (−2, −1) | 0.0106 | 1.8931 | (2, 1) | −0.0145 | −1.9597 |
| (−2, 0) | 0.0014 | 1.4637 | (2, 0) | −0.0039 | −1.7022 |
| (−2, 1) | −0.0071 | 1.0695 | (2, −1) | 0.0073 | −1.4099 |
| (−2, 2) | −0.0150 | 0.7107 | (2, −2) | 0.0193 | −1.0827 |
| (−1, −2) | 0.0212 | 1.5870 | (1, 2) | −0.0211 | −1.3694 |
| (−1, −1) | 0.0107 | 1.1563 | (1, 1) | −0.0117 | −1.1123 |
| (−1, 0) | 0.0010 | 0.7607 | (1, 0) | −0.0017 | −0.8203 |
| (−1, 1) | −0.0080 | 0.4004 | (1, −1) | 0.0091 | −0.4934 |
| (−1, 2) | −0.0164 | 0.0752 | (1, −2) | 0.0206 | −0.1315 |
| (0, −3) | 0.0329 | 1.1893 | (0, 3) | −0.0266 | −0.8739 |
| (0, −2) | 0.0212 | 0.7579 | (0, 2) | −0.0184 | −0.6175 |
| (0, −1) | 0.0102 | 0.3614 | (0, 1) | −0.0095 | −0.3263 |
| (0, 0) | 0.0000 | 0.0000 | | | |

Therefore, the system composed of the off-axis parabolic mirror and planar mirror can also maintain the polarization characteristics of polarized light.

The above only exemplifies the condition of replacing one of the two planar mirrors with an off-axis parabolic mirror with the same reflective material and the same coating structure. Those skilled in the art should understand that, not only planar mirror and off-axis parabolic mirror, but also other curved mirrors, such as toroidal mirror, ellipsoidal mirror or non-quadric surface mirror, can substantially maintain the polarization characteristics of polarized light as long as any two of mirrors meet the above relations.

Figure 7:
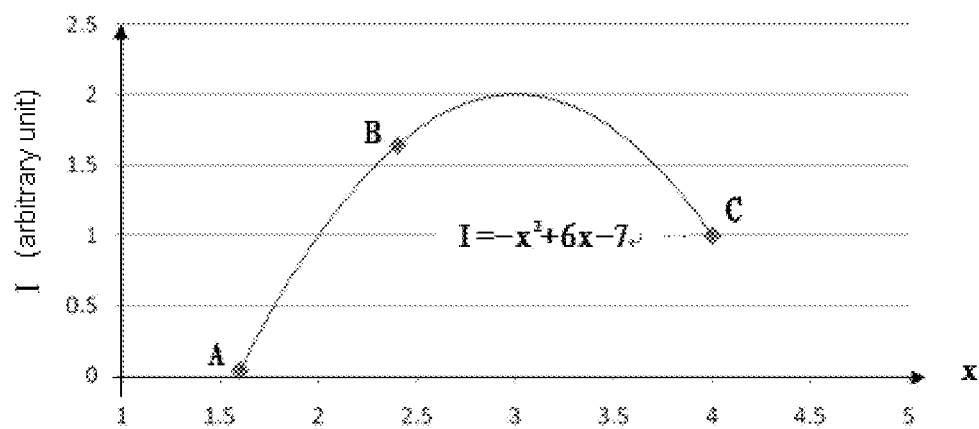
FIG. 7 is a schematic drawing for explaining a mathematical method of quickly finding a focus point.

In summary, if the two mirrors have approximately the same reflective material and approximately the same coating shown in FIG. 7, according to measurement value of the first three different positions (i.e., A, B and C position), the maximum position of the quadratic curve can be obtained by curve fitting; take the measured value from this position as the newly added data point, and fit curve again; iterate this procedure until the fitting meets the formula $|x_{n+1}-x_n|<\sigma$ theoretically, where $x_n$ is the focusing position of the nth time, $x_{n+1}$ is the focusing position of curve fitting of (n+1)th time obtained when the measured value at the focus position of nth times is added, and σ is the adjustable accuracy of the system.

The second method is to observe the definition of imaging of the sample surface in the pattern recognition system to achieve focus. In an ideal focus state, after the position of pattern recognition system is calibrated, the image shall be the clearest if the sample surface is in focus. For a given image resolution, the image definition is determined by the sharpness of image. The sharpness was the contrast of the image edge. More precisely, the sharpness is the amplitude of the brightness derivative in space. After the coarse focus was achieved, (i.e., the sample surface can be identified in pattern recognition system), the image definition can be simultaneously calculated through the focus adjustment. So, with the assistance of above mathematical methods and the basic steps of quickly finding the focus point, the most accurate focus can be obtained.

Figure 8:
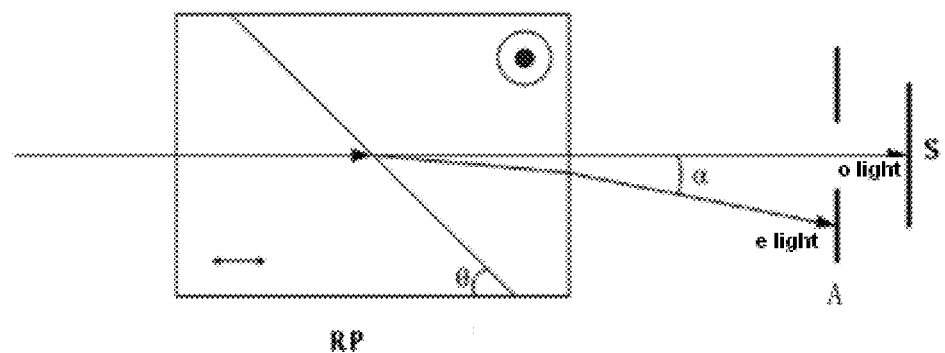
FIG. 8 is an optical schematic drawing of a Rochon prism polarizer, in which RP represents the Rochon prism polarizer, A represents an aperture, and S represents a sample.

For the polarizer adopted in the invention, a Rochon prism polarizer RP as shown in FIG. 8 can be adopted. The material of the Rochon prism polarizer can be $MgF_2$, a-BBO, Calcite, $YVO_4$ or quartz. By using birefringent crystal (the refractive indices of o light and e light are different), Rochon prism polarizer makes the two polarized beams in the orthogonal direction of incident beam exit from Rochon prism interface with a certain angle, where the direction of o light remains the same as the incident direction, and exits with the state of linearly polarized light. Different materials have different transmission spectral range; for $MgF_2$ the spectral range can be up to 130-7000 nm. Since the refractive indices of o light and e light are different for different materials, the angle between the o light and e light of transmitted light is different as well. For example, for $MgF_2$ or quartz, the angle difference between o light and e light is 1-2 degrees, however, for the a-BBO or $YVO_4$, the angle is up to 8-14 degrees. This angle also partly depends on the cutting angle θ of the Rochon prism. After the probing beam transmitted through the polarizer, the o light has the angle of incident normal to the sample, whereas the e light is at an oblique incident angle α on the sample; when the reflected beam of the e light from the sample surface enters into the range of the optical aperture of the polarizer, the reflected beam of the e light may enter into the same polarizer at the same time, and then reaches the probe, thus affects the measurement. For a polarizer with large e light deviation angle, the reflected beam of the e light from the sample surface is hard to re-enter the polarizer. In order to improve the measurement accuracy and avoid the influence of the reflected beam of the e light, an aperture A (as shown in FIG. 8) can be provided at a position above the sample surface where the o light and e light are separated to avoid the e light from being incident on the sample surface or the reflected beam of the e light from being reflected back to the polarizer from the sample surface.

Figure 9A:
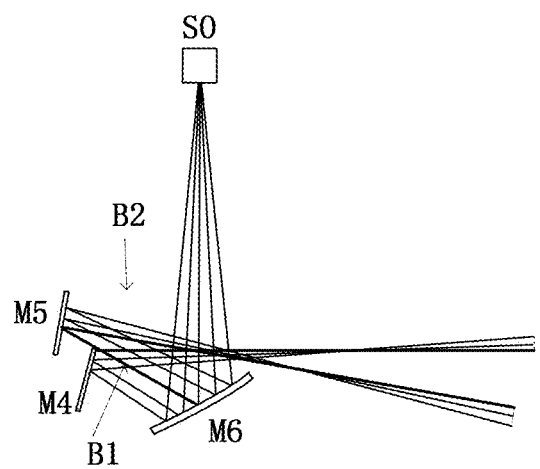
FIG. 9a and FIG. 9b are schematic drawings of the realization of the beam combining through two non-coplanar planar mirrors of the invention.
Figure 9B:
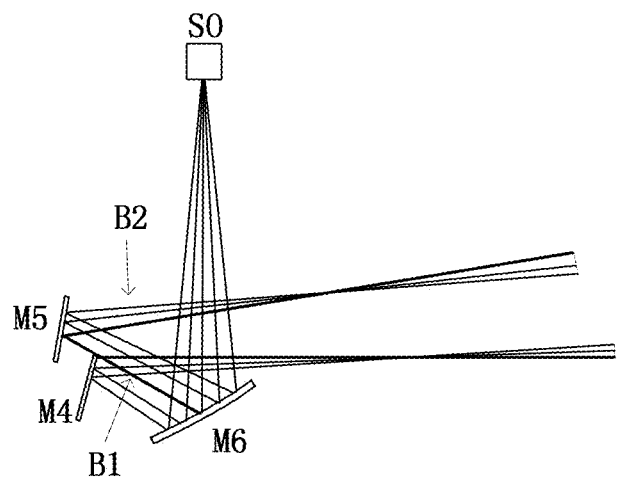

Hereinafter, the process of realizing beam splitting and beam combining through the first reflecting unit and the second reflecting unit containing two non-coplanar planar mirrors respectively with reference to FIG. 9a, FIG. 9b and FIG. 10.

(1) Realizing beam splitting: As shown in FIG. 9a, assuming that divergent beam from spot light source forms a focused beam after passing through the light source concentrating unit, e.g., curved mirror M6, and is deflected within an incident plane to be incident on the first reflecting unit. The first reflecting unit is composed of two non-coplanar planar mirrors M4 and M5. The planar mirror M4 contains a straight edge, and the straight edge is in the optical path of the focused beam. One half of the focused beam is incident on the planar mirror M4, and deflected within the incident plane after being reflected by the planar mirror M1 to form a focused beam B1. The other part of the focused beam passes through the straight edge of the planar mirror M1, is incident on the planar mirror M5, and deflected within the incident plane after being reflected by the planar mirror M5 to form a focused beam B2. The main axis direction of the planar mirror M5 is slightly inclined relative to the planar mirror M4 within the incident plane, so that the main beams of the focused beams B1 and B2 reflected by the planar mirrors M4 and M5 respectively first are intersected with each other, than separated, as shown in FIG. 9a, or the focused beams B1 and B2 are separated directly, as shown in FIG. 9b. Since then, the light from the spot light source passes through the first reflecting unit, i.e., the planar mirrors M4 and M5, then be split into two beams used as the probing beam and the reference beam respectively. Before and after beam splitting, the main beams of the two beams are always in the same plane, and the straight edge of the planar mirror M5 is perpendicular to the plane.

(2) Realizing beam combining: As shown in FIG. 10, when the probing beam reflected by the sample returns to the plane where the reference beam is in along the same path, it is the focused beam. The second reflecting unit is composed of two non-coplanar planar mirrors M2 and M3. The probing beam and the reference beam returned from the sample surface inject on the planar mirror M2 and the planar mirror M3 constituting the second reflecting unit respectively. The planar mirror M2 contains at least one straight edge, and the straight edge intersects with the main beam of the probing beam. The probing beam is incident on and focused on the spectrometer SP after being reflected by the planar mirror M2. The spectrometer SP is placed at the focus point of the focused probing beam. The reference beam within the same plane becomes a focused beam after passing through the lens L or other concentrating elements, such as reflection objective, then is reflected by the planar mirror M2, deflected within the incident plane and incident on the same spectrometer SP. By rotating the planar mirror M3 and/or moving the planar mirror M3 along the direction of the light (or reverse direction), the propagation direction and/or deflection position of the reference beam can be changed, thus to overlap the main beam of the reference beam and the main beam of the probing beam, and the reference beam and the probing beam do not influence each other. The focusing position of the reference beam can be adjusted by moving the converging lens L (not shown in figure) along the direction of reference beam (or reverse direction). That is, adjusting the planar mirror M3 and the focusing lens L can make the reference beam incident on and focused on the same spectrometer SP. Since then, the probing beam and the reference beam from different directions can be incident on and focused on the same spectrometer SP after being reflected by the second reflecting unit.

Figure 10:
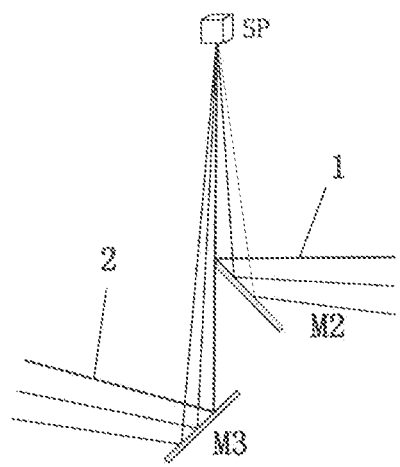
FIG. 10 is a schematic drawing of the realization of the beam combining through two non-coplanar planar mirrors of the invention.
Figure 11A:
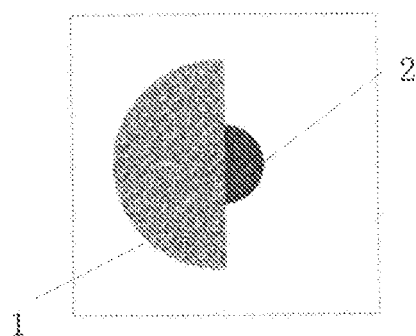
FIG. 11a and FIG. 11b are images formed by beam cross section shape after light combining through simulation and beam.
Figure 11B:
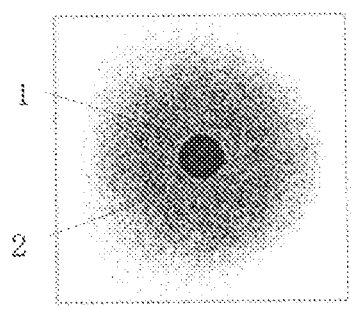

According to the beam combining process shown in FIG. 10, the cross section of the probing beam 1 and the reference beam 2 obtained by simulation is as shown in FIG. 11a after being reflected by the second reflecting unit. By suitable design of optical path, the probing beam 1 and the reference beam 2 are incident on the same spectrometer and probed simultaneously, and during the process, the probing beam 1 and the reference beam 2 propagate without influencing each other. The images formed by the probing beam 1 and the reference beam 2 focusing on the spectrometer are shown in FIG. 11b. In FIG. 11b, the sizes of the focusing spots on the spectrometer formed by the probing beam 1 and the reference beam 2 are different from each other, this is because the amplification ratio is different during two beam focusing. During actual probing, it is necessary to select an entrance slit of suitable size for the spectrometer, so that the reference beams are probed as many as possible, thus to increase the signal to noise ratio of the reference beam for the measurement accuracy improvement purpose.

Since the planar mirror itself does not influence the converging state of the incident light and does not produce chromatic aberration, the mirror can change the propagation direction of the beam while ensuring the quality of focused beam. The probing beam and the reference beam can be focused on the same spectrometer simultaneously after passing through the two planar mirrors. On the other hand, the planar mirror can realize high reflectivity within the broadband spectral range, and has little influence on the light intensity. The design of the one spectrometer of the invention does not reduce the probing efficiency of the spectrometer to the probing beam and the reference beam. Therefore, the invention, by suitable design of optical path, achieves an integral combination of the light beams after splitting, increases the light transmission efficiency, and has a lower complexity than that in the prior art.

In the invention, an absolute reflectivity measurement method is adopted, i.e., the absolute reflectivity of sample in two orthogonal directions of polarization state is measured. The absolute reflectivity of a sample can be measured as follows:

a. The dark values $I_{d0}$ of a spectrometer is measured, i.e., the readings of the spectrometer when a dark signal enters the spectrometer.

b. A reference sample is loaded, e.g., bare silicon wafer, to obtain the spectral numerical value $I_{Si0}$, and the spectral numerical value $I_{Si0}$ of the reference beam is measured immediately before or after measuring the reference sample.

c. The sample to be tested is loaded and measured to obtain the spectral numerical value I, and the spectral numerical value $I_R$ of the reference beam is measured immediately before or after measuring the sample to be tested.

d. The dark values $I_d$ of a spectrometer is measured.

In the above steps, the steps a and b are only needed to operate once for a period of time, for example, within one hour, within one day, one week or several weeks. The steps c and d should be re-operated during each measurement. If the environment temperature keeps constant, or the dark value of the spectrometer does not change with time, $I_d$ can be replaced with $I_{d0}$.

In this way, the reflectivity of the sample is:

$$R = \frac{I - I_d}{(I_{Si0} - I_{d0})f(r)} R(Si0) = \frac{I - I_d}{(I_{Si0} - I_{d0})\left(\frac{I_R - I_d}{I_{R0} - I_{d0}}\right)} R(Si0)$$

where, R(Si0) is the absolute reflectivity of the reference sample. R(Si0) can be obtained from other measurements, or through calculating the characteristics of the reference sample, usually from the reflectivity of bare silicon wafer;

$$f(r) = \frac{I_R - I_d}{I_{R0} - I_{d0}}$$

is the correction of measurement error caused by light source fluctuation by the reference beam.

Figure 12:
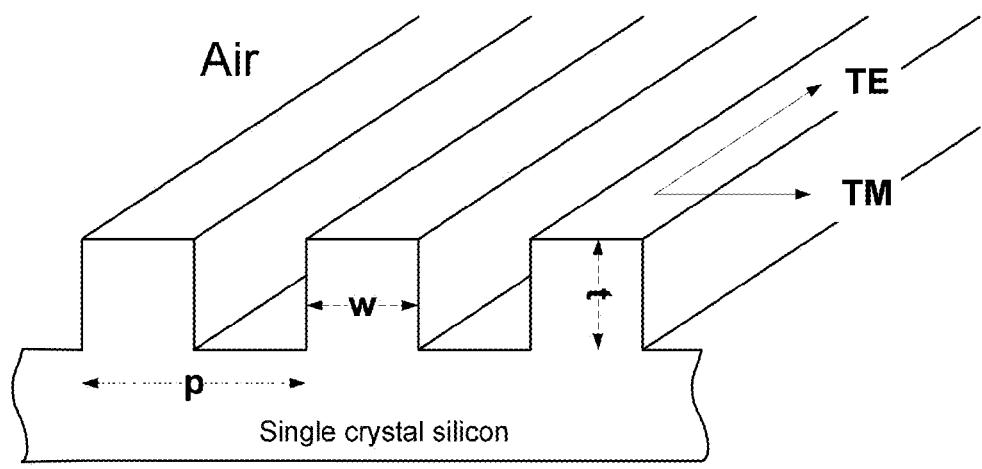
FIG. 12 is a structure diagram of periodic shallow trench on a single crystal silicon.
Figure 13:
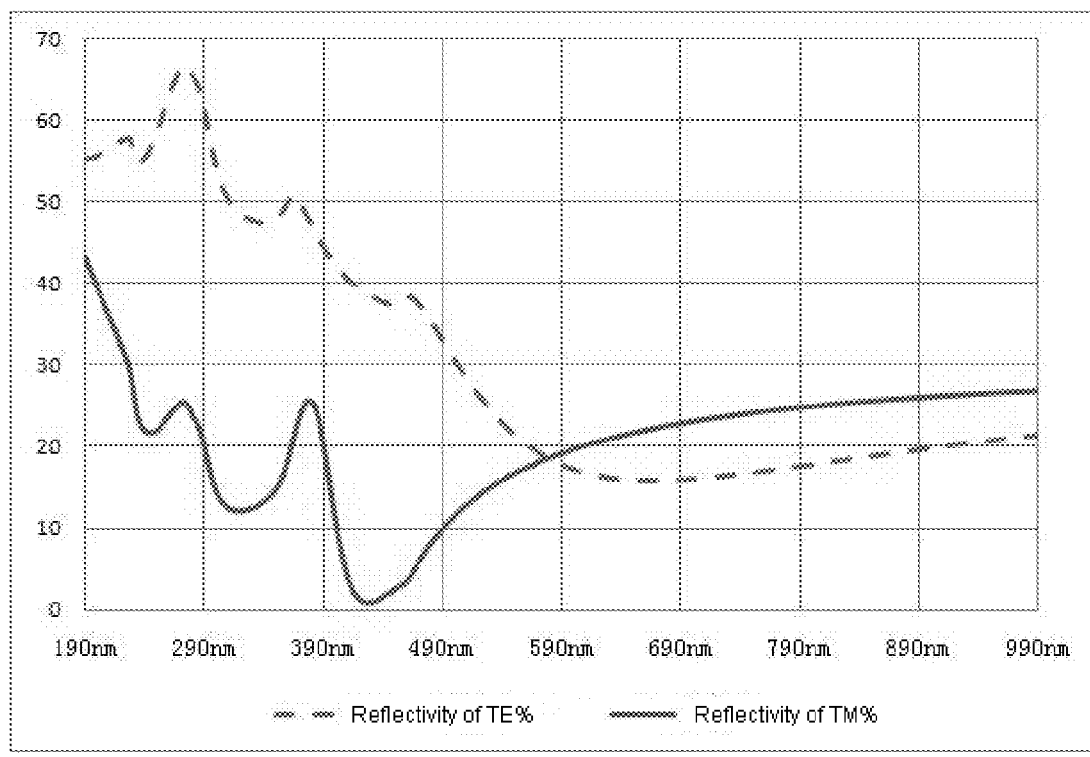
FIG. 13 is a schematic drawing to show the absolute reflectance spectra of TE and TM modes from the single crystal silicon periodic shallow trench in an absolute reflectivity measurement method.

For example, in a periodic shallow trench structure, as shown in FIG. 12, the two orthogonal polarization directions are defined respectively as the direction perpendicular to the linear structure of TM and the direction parallel to the linear structure of TE. When a pitch is 100 nm, a line width w is 50 nm, and a trench depth t is 50 nm, the reflectivity is as shown in FIG. 13, wherein the dotted line is the reflectivity of TE polarization direction, the solid line is the reflectivity of TM polarization direction.

After the TE and TM absolute reflectivity is obtained by measurement, the critical dimension and three-dimensional profile of the periodically patterned sample surface, and film thickness and optical constants of multilayer materials can be derived, by comparing the measurements with the numerical simulation results through numerical regression. In this case, the normal-incidence broadband spectroscopic polarimeter can also include a calculating unit; the calculating unit is used for calculating the optical constants and film thickness of the sample and/or analyzing the critical dimension characteristics or three-dimensional profiles of the periodic structure of the sample by mathematical model calculation and curve regression fit of the reflectivity. At present, the common method for electromagnetic wave simulation and calculation of a periodic structure is Rigorous Coupled-Wave Analysis (RCWA), and the regression algorithm is Levenberg-Marquardt algorithm. In the invention, besides the theoretical methods for measurement, the measurement process also involves processing the variations caused by polarization sensitivity such as polarizer rotation. Such problems can be resolved by numerical method, more detailed description can be referred to U.S. Pat. No. 6,522,406B1 and U.S. Pat. No. 6,665,070B1. In the invention, the linear polarization direction of the beam passing through polarizer is determined by the polarizer rotation angle; the light source entering the polarizer can be a beam in arbitrary polarization state. The light reflected by sample is a linear polarized light after passing through the polarizer. In the process that the beam is incident onto the detector, the light reflected by the reference samples and the light reflected by the measuring samples are experiencing the same change of polarization, so it is not required to keep polarization state and thus the polarization sensitive components in the optics are not restricted.

The invention is described in detail below by taking the embodiments as example.

Embodiment I

Figure 14A:
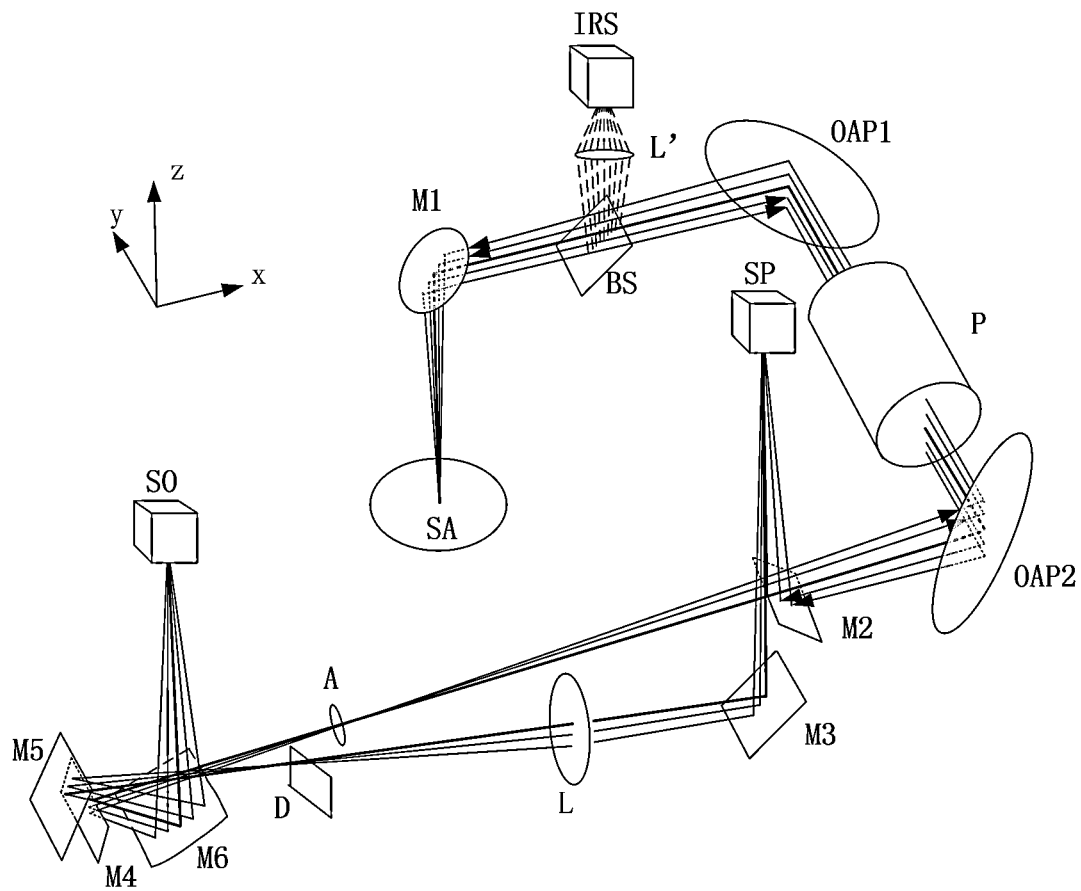
FIG. 14a is a schematic drawing illustrating a normal-incidence broadband spectroscopic polarimeter according to the first embodiment of the invention.

A normal-incidence broadband spectroscopic polarimeter according to the first embodiment of the invention is shown in FIG. 14a. As shown in FIG. 14a, the normal-incidence broadband spectroscopic polarimeter includes a broadband spot light source SO, a first reflecting unit (including planar mirrors M4 and M5), a moveable light blocking plate D, an aperture A, a first concentrating unit (an off-axis parabolic mirror OAP2), a polarizer P, a first off-axis parabolic mirror OAP1, a first planar mirror M1, a second concentrating unit (lens L), a second reflecting unit (including planar mirrors M2 and M3), a broadband spectrometer SP, a movable beam splitting plate BS (refer to FIG. 14b for specific position thereof) and a pattern recognition system IRS. The pattern recognition system IRS includes a lens L', an illumination light source (not shown) and a CCD imager (not shown). The broadband spot light source SO can emit divergent beam containing a broadband spectrum. The broadband spectrum is usually in the deep ultraviolet to near infrared range (from about 190 nm to 1100 nm wavelength range). In practice, the broadband spot light source SO can be a xenon lamp, a deuterium lamp, a tungsten lamp, a halogen lamp, a mercury lamp, a composite broadband light source including deuterium lamp and tungsten lamp, a composite broadband light source including tungsten lamp and halogen lamp, a composite broadband light source including mercury lamp and xenon lamp or a composite broadband light source containing deuterium lamp, tungsten lamp and halogen lamp. The beam emits from the broadband light source can be natural light (i.e., the degree of polarization equal to zero). However, the broadband spot light source can be a spot light source of natural light with a degree of polarization equal to zero produced by polarizer. Examples for broadband spot light source SO include Ocean Optics products HPX-2000, HL-2000 and DH2000, and Hamamatsu company product L11034, L8706, L9841 and L10290. The broadband spectrometer can be charge-coupled device (CCD) or photodiode array (PDA), for example, the Ocean Optics QE65000 spectrometer, or the B&W TeckCypher spectrometer. Examples of the pattern recognition system IRS includes EDMUND Company product NT59-839, NT59-743, SEIWA company FVL-5X-120D-C, FVL-6X-120D-C, Canrui Optical Company product XF-T6X-110D, etc.

The divergent beam emitted from the broadband spot light source SO is incident on the planar mirrors M3 and M4 and split into two beams, one of which is a probing beam, and the other is a reference beam. As a preferred embodiment, it also includes a light source concentrating unit (curved mirror M6). The beam emitted from the broadband spot light source SO propagates in a vertical plane and is incident on the curved mirror M6 to form a focused beam. The first reflecting unit, i.e., the planar mirrors M4 and M5, splits the focused beam into two beams, one of which is a probing beam, and the other is a reference beam. The optical paths of the two beams are described below respectively:

(1) the focused beam of the main beam reflected by M4 within the horizontal plane is used as a probing beam, and the aperture A is placed at the focus point of the focused beam. The probing beam passing through the aperture is diverged again and incident on the first concentrating unit, i.e., the off-axis parabolic mirror OAP2. If the focus point of the off-axis parabolic mirror OAP2 is coincident with the focus point of the divergent beam, the divergent beam is reflected by the off-axis parabolic mirror OAP2 to form a parallel beam along the horizontal direction. The parallel beam is incident on the first off-axis parabolic mirror OAP1 after passing through the polarizer P. The first off-axis parabolic mirror OAP1 rotates the parallel beam by 90 degrees within the horizontal plane. The beam reflected by the first off-axis parabolic mirror OAP1 is a focused beam with main light in the horizontal plane. After being reflected by the planar mirror M1, the focused beam is incident on and focused on the sample surface along the vertical direction. The light reflected from the sample surface, passing through the first planar mirror M1, the first off-axis parabolic mirror OAP1, the polarizer P, the off-axis parabolic mirror OAP2 in order, forms a focused beam. The focused beam, after being reflected by the planar mirror M2, is incident on the broadband spectrometer SP perpendicularly upward. The broadband spectrometer SP is placed at the focus point of the probing beam converged after being reflected by the planar mirror M2. (2) The light passing through the edge of the planar mirror M4 and reflected by the planar mirror M5 is used as a reference beam. The planar mirror M5 is slightly inclined relative to M4. The reference beam reflected by the planar mirror M5 is intersected with the probing beam reflected by the planar mirror M4, and then separated. The reference beam becomes a divergent beam after being converged to one point. The divergent beam is incident on the second concentrating unit, i.e., the concentrating lens L, to form the focused beam, which is incident on the broadband spectrometer SP perpendicularly upward after passing through the planar mirror M3.

Those skilled in the art should understand that the reference beam can be incident on the spectrometer SP perpendicularly by adjusting and/or rotating the planar mirror M2, and the reference beam can be focused on the spectrometer SP after being reflected by the planar mirror M2 by moving the position of the concentrating lens L2 along or against the incident direction of the reference beam.

In the embodiment of the invention, the probing beam and the reference beam are within the same plane P1, before the probing beam is emitted from the broadband light source SO to off-axis parabolic mirror OAP2, and before leaving the off-axis parabolic mirror OAP2 to the broadband spectrometer SP after reflected by sample, and before the reference beam is emitted from the broadband light source SO to the broadband spectrometer SP. The probing beam is within the plane P2 perpendicular to the plane P1 before reaching the planar mirror M1 after reflected by the planar mirror M4, and before leaving the planar mirror M1 to the planar mirror M2 after reflected by sample.

Figure 1:
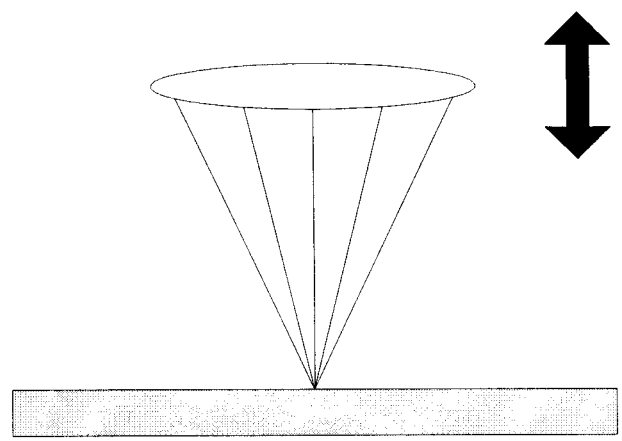
FIG. 1 is a schematic drawing illustrating the realization of the focus by moving the last focusing lens up and down in the prior art.
Figure 2:
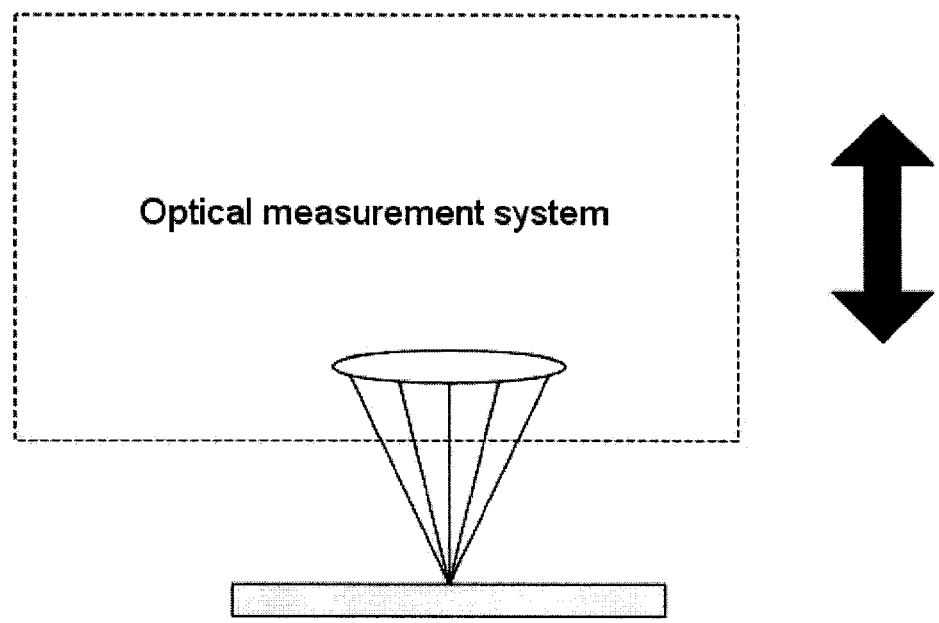
FIG. 2 is a schematic drawing illustrating the realization of the focus by moving the entire optical system up and down in the prior art.
Figure 3A:
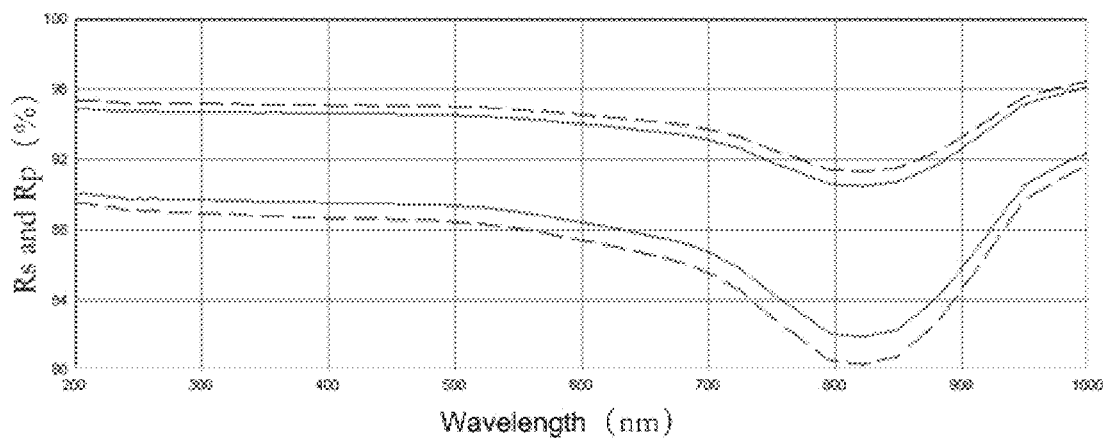
FIG. 3a illustrates that the reflectivity of S and P polarized light reflected by a mirror made of aluminium changes with an angle of incident light, where the above two curves correspond to the S polarized light, and the below two curves correspond to the P polarized light.
Figure 3B:
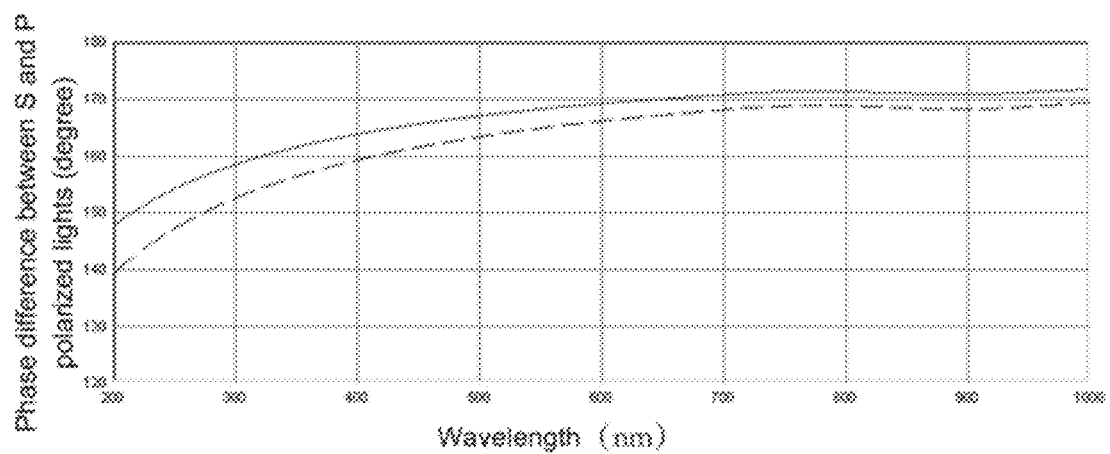
FIG. 3b illustrates that the phase difference of S and P polarized light reflected by a mirror made of aluminium changes with an incident angle.
Figure 4:
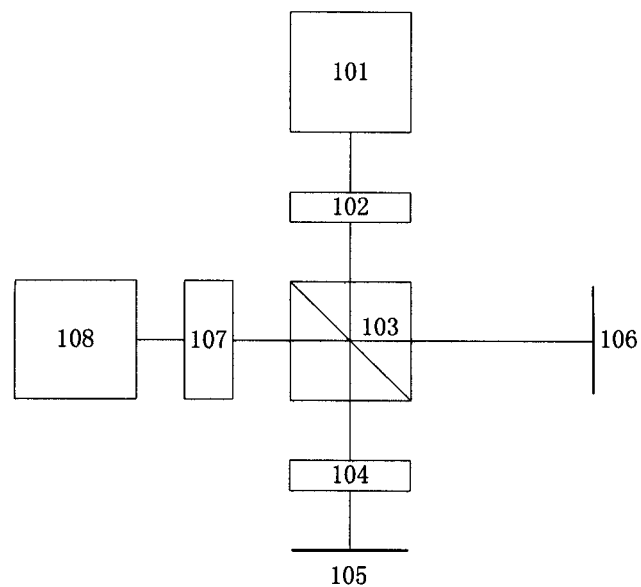
FIG. 4 is a schematic drawing of realization of beam splitting and beam combining by a beam splitter in the prior art.

In the invention, the light emitted from the spot light source is split into the probing beam and the reference beam after passing through the first reflecting unit (i.e., reflected by the planar mirrors M4 and M5). The probing beam and the reference beam returned from the sample surface are combined into a beam with a cross section shape as shown in FIG. 4a after passing through the second reflecting unit (i.e., the planar mirrors M2 and M3), thus to realize the purpose that the probing beam and the reference beam share one spectrometer.

In the invention, a moveable baffle D can be moved automatically or manually to cut off the reference beam and/or probing beam. Moreover, when the moveable baffle D is not in the optical path of the probing beam and/or reference beam, there is no influence on the corresponding optical path. After beam switching, spectral measurement can be performed without re-adjusting the optical path. So, the normal-incidence broadband spectroscopic polarimeter of the invention can simply realize fast switching between the reference beam and the probing beam during measurement.

In the invention, the polarizer can be a thin-film polarizer, Glan-Thompson prism polarizer, Rochon prism polarizer, Glan-Taylor prism polarizer, and Glan laser polarizer. In particular, the preferred polarizer is a Rochon prism polarizer and its material is preferred to be magnesium fluoride ($MgF_2$). In the embodiment, the beam splitting plate BS and the mirrors M2 and M4 are planar reflecting elements, such as semicircular planar mirrors or square mirrors, which at least contain one straight edge. Those skilled in the art should understand that the straight edges of the beam splitting plate BS, and the planar mirrors M2 and M4 are parallel to one another, and the straight edges intersect with the main light of the beam. The straight edge preferably has an acute angle to avoid reflecting the reference beam.

Furthermore, the inclination angle and/or spatial position of the planar mirror M1 is adjustable, for example, can be move along the propagation direction of the main light of the focused beam from the off-axis parabolic mirror OAP1. Likewise, the broadband spectrometer can also include an adjustable sample platform for loading the sample. According to the above focusing principles, those skilled in the art will understand how to realize focusing by adjusting the planar mirror M1.

Furthermore, the normal-incidence broadband spectroscopic polarimeter of the invention may also include a polarizer rotation controlling device, which is used for controlling the rotation of the polarizer to adjust the polarization direction of the beam. The polarizer rotation controlling device can adopt various automatic rotation devices controlled by a motor (measurement can also be realized manually), for example, Newport Precision Rotation Stage URS 150.

The measured sample is often placed on an adjustable sample stage, such as X-Y-Z-Theta or R-Theta-Z workbench. In the semiconductor industry, the sample size is often a diameter of 8 inches (200 mm), or 12 inches (300 mm) wafer. In the flat panel display industry, the samples usually have a size of more than one meter. Due to the reasons such as film stress on wafer, the wafers may be uneven. For a large-scale sample, the sample surface may be distorted, or the sample platform may be uneven. Therefore, each measurement point needs to be refocused when the samples are tested in order to realize high accuracy measurement and ensure rapid measurement of high throughput of semiconductor production line.

Figure 14B:
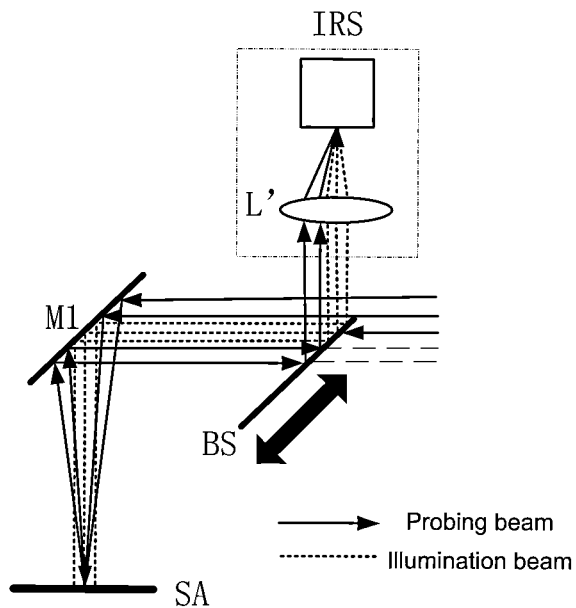
FIG. 14b is a schematic drawing to show an optical path where the sample surface and the probing beam are focused and imaged by the beam splitter and a pattern recognition system.
Figure 15A:
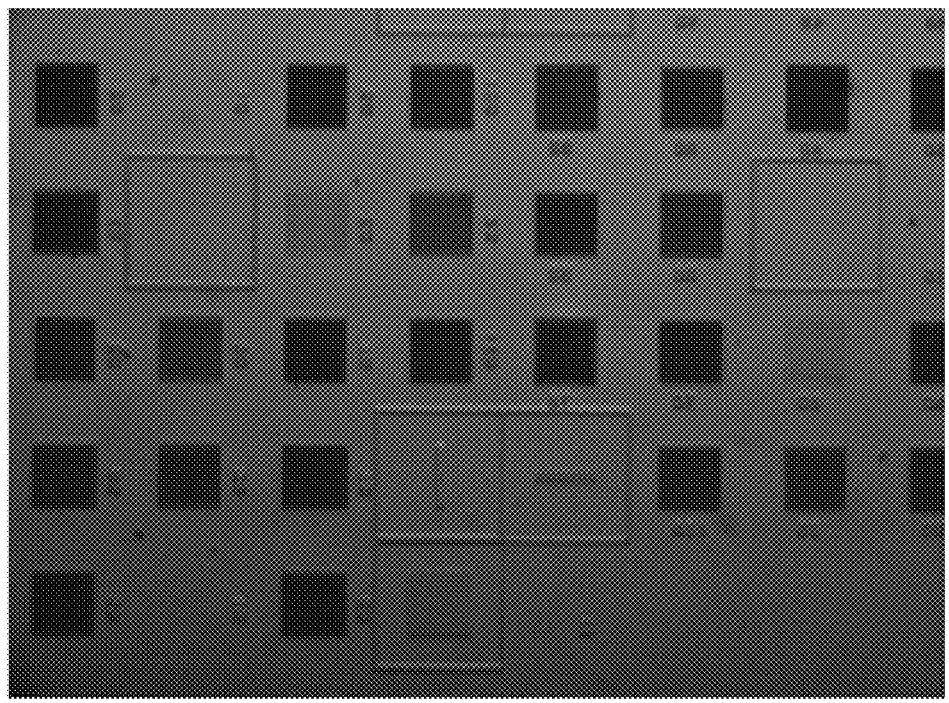
FIG. 15a and FIG. 15b are patterns observed by the pattern recognition system.
Figure 15B:
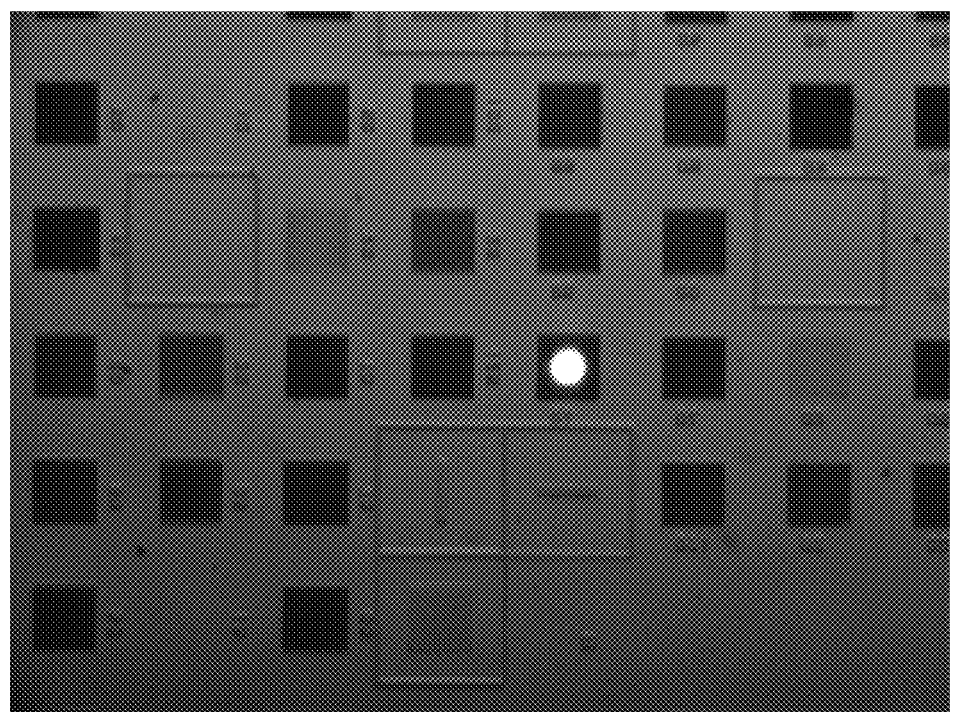

Before measuring the sample, it is necessary to recognize and locate the measurement point on the sample surface by the pattern recognition system. This process can be realized in a way that the beam splitter moves into the optical path along the direction as shown by the arrow in FIG. 14b. Specific operation is as follows: the moveable beam splitting plate is moved into the optical path of the probing beam (including a sample reflected beam of the probing beam), the non-reflecting surface completely covers the probing beam, and the reflecting surface makes the illumination beam incident on the sample surface. At this time, the pattern on the sample surface can be imaged in a CCD imaging system. A chip sample surface pattern as shown in FIG. 15a can be obtained in the CCD imaging system by adjusting the focus of the sample by calculating the imaging definition on the sample surface based on the calibrated pattern recognition system IRS. The darker square area in the figure is the measurement point. After the measurement point is recognized, the beam splitting plate can be moved away from the optical path of the probing beam partly, the non-reflecting surface partly covers the probing beam, and the reflecting surface makes the illumination beam incident on the sample surface, while making the probing beam and the illumination beam reflected by the sample surface to the CCD imaging system, the optical path of which is as shown in FIG. 14b. At this time, the probing beam and the pattern on the sample surface can be imaged in the CCD imaging system, thereby aligning the light spot and the measurement point through the moveable sample platform. When the light spot and the measurement point are aligned, the image observed in the CCD imaging system is as shown in FIG. 15b. The bright spot in the centre is the image formed by the probing beam. After the above steps are finished, the measurement point can be measured. During measurement, the beam splitting plate BS needs to be moved away from the optical path of the probing beam completely (at this time, there is no image in the CCD), so that the probing beam freely propagates to the sample surface to perform spectral measurement.

Furthermore, the invention also provides another focus judgment method, i.e., adjusting the focus by observing the imaging definition in the pattern recognition system IRS, besides judging the focus by observing the change of light intensity in the spectrometer. The coexistence of two focusing system improves the focus accuracy of the equipment. it is possible to realize the function of aligning the light sport of the probing beam on the sample surface and the pattern on the sample surface. Moreover, during focusing process, the movable beam-splitting plate BS does not need to be adjusted with the position of the planar mirror M1.

According to the embodiment, those skilled in the art should understand that, if the planar mirror M1 and the off-axis parabolic mirror OAP1 have the same reflective material and the same coating structure and meet the conditions that incident angles of the beam are the same and the incident planes are perpendicular to each other, the polarization characteristics of the probing beam at the time of reaching the sample surface remain unchanged relative to when leaving the polarizer when the probing beam propagates in the optical path between the polarizer and the sample surface, and the polarization characteristics of the reflected light (i.e., elliptically polarized light) of the sample at the time of returning to the polarizer also remain unchanged relative to when leaving the sample. That is, when the beam propagates between the polarizer and the sample surface, the polarization characteristics are changed only due to the reflection from the sample. That is, in the invention, the focusing system and the focusing process does not affect the beam polarization state. The normal-incidence broadband spectroscopic polarimeter with double beam can measure the anisotropic thin-film sample or non-uniform thin-film sample such as its the critical dimensions (CD) and three-dimensional profile of the periodic pattern of the surface, film thickness and optical constants of the multilayer material by using the two measurement methods as described above.

In the embodiment, the linear polarization direction of the probing beam passing through the polarizer is determined by the polarizer rotation angle and the beam incident on the polarizer can be a beam in an arbitrary polarization state. The beam reflected by the sample and passed through the polarizer is linearly polarized light; in this process, the light reflected by the reference samples and the light reflected by the measuring samples experience the same change of polarization state when the beam is incident on the probe. So it is not required to maintain the polarization state and there is no restriction on the polarization sensitivity of optical components.

The use of the normal-incidence broadband spectroscopic polarimeter of the embodiment not only performs focusing by simple operation and accurately controls the polarization change of the probing beam (i.e., can maintain the polarization characteristics of any polarized light), but also can correct the measurement error caused by the change of spectrum of the broadband light source during the measurement of the absolute reflectivity method by simple operation. Furthermore, since only one spectrometer is needed, the cost is not increased.

Any other equivalent forms of the embodiment can occur to those skilled in the art according to the embodiment and the above principles to maintain the polarization characteristics as well as the method of realizing beam splitting and beam combining of the planar mirror.

Embodiment II

Figure 16:
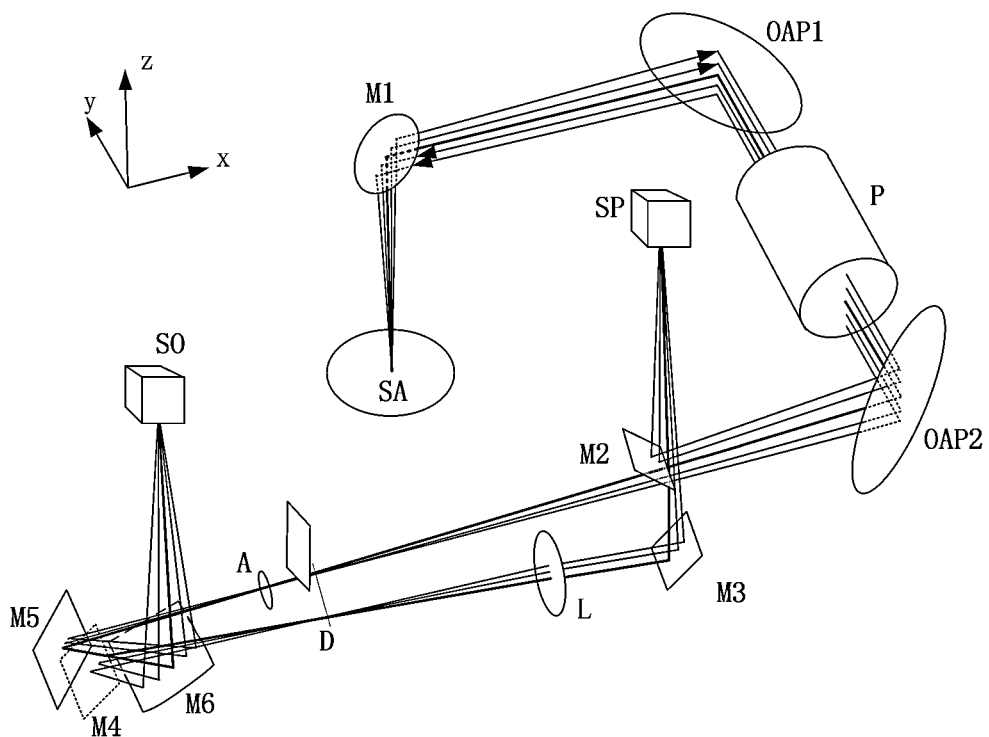
FIG. 16 is a schematic drawing illustrating a normal-incidence broadband spectroscopic polarimeter according to the second embodiment of the invention.

An optical path diagram of normal-incidence broadband spectroscopic polarimeter according to the second embodiment of the invention is shown in FIG. 16. The optical path element and measurement method of the embodiment are substantially the same as the normal-incidence broadband spectroscopic polarimeter with double beam according to the first embodiment of the invention, but the optical path characteristics are slightly different. For simplicity, only the optical path is described briefly.

The beam emitted from the broadband spot light source SO is reflected by the curved mirror M6 to form a focused beam. The first reflecting unit, i.e., the planar mirrors M4 and M5, splits the beam into a probing beam and a reference beam. The second reflecting unit, i.e., the planar mirrors M2 and M3, combines the probing beam and the reference beam returned from the sample surface into a beam, then makes it incident on the same spectrometer SP. Unlike the first embodiment, the beam reflected by M4 is a reference beam, the beam reflected by M5 after passing through the edge of M4 is a probing beam. In the embodiment, the reference beam and the probing beam are not intersected with each other after passing through the two mirrors, but separated directly. The reference beam is converged to one point to be a divergent beam. The divergent beam is incident on the second concentrating unit (concentrating lens L) to form a focused beam. The focused beam is incident on the broadband spectrometer SP perpendicularly after being reflected by the planar mirror M3. The beam passing through the edge of M5 and reflected by M4 is the probing beam. The probing beam is a focused beam with main light in the horizontal plane. The aperture A is placed at the focus point of the focused beam. The probing beam passing through the aperture is diverged again and incident on the first concentrating unit (the off-axis parabolic mirror OAP2). The divergent beam is reflected by the off-axis parabolic mirror OAP2 to deflect 90 degrees to form a parallel beam along the horizontal direction. The parallel beam is incident on the first off-axis parabolic mirror OAP1 after passing through the polarizer P. The first off-axis parabolic mirror OAP1 rotates the parallel beam by 90 degrees within the horizontal plane to form a focused beam. The focused beam is focused on the sample surface after being reflected by the planar mirror M1, and the main light is incident on the sample surface perpendicularly. The light reflected from the sample surface, passing through the first planar mirror M1, the first off-axis parabolic mirror OAP1, the polarizer P, the off-axis parabolic mirror OAP2 in order, forms a focused beam. The focused beam, after being reflected by the planar mirror M2, is incident on the broadband spectrometer SP perpendicularly after deflecting 90 degrees within the incident plane. The broadband spectrometer SP is placed at the focus point of the probing beam converged after being reflected by the planar mirror M2.

Those skilled in the art should understand that the reference beam can be incident on the spectrometer SP perpendicularly by adjusting and/or rotating the planar mirror M2, and the reference beam can be focused on the spectrometer SP after being reflected by the planar mirror M2 by moving the position of the concentrating lens L2 along or against the incident direction of the reference beam.

Like the first embodiment, the probing beam and the reference beam are within the same plane, before the probing beam is emitted from the broadband light source SO to off-axis parabolic mirror OAP2, and before leaving the second off-axis parabolic mirror OAP2 to the broadband spectrometer SP after reflected by sample, and before the reference beam is emitted from the broadband light source SO to the broadband spectrometer SP. The probing beam is within the same plane before reaching the planar mirror M1 after reflected by the planar mirror M4, and before leaving the planar mirror M1 to the planar mirror M2 after reflected by sample.

The embodiment can also add the pattern recognition system as in the first embodiment.

The embodiment can implement the same measurements described in the first embodiment.

Embodiment III

Figure 17:
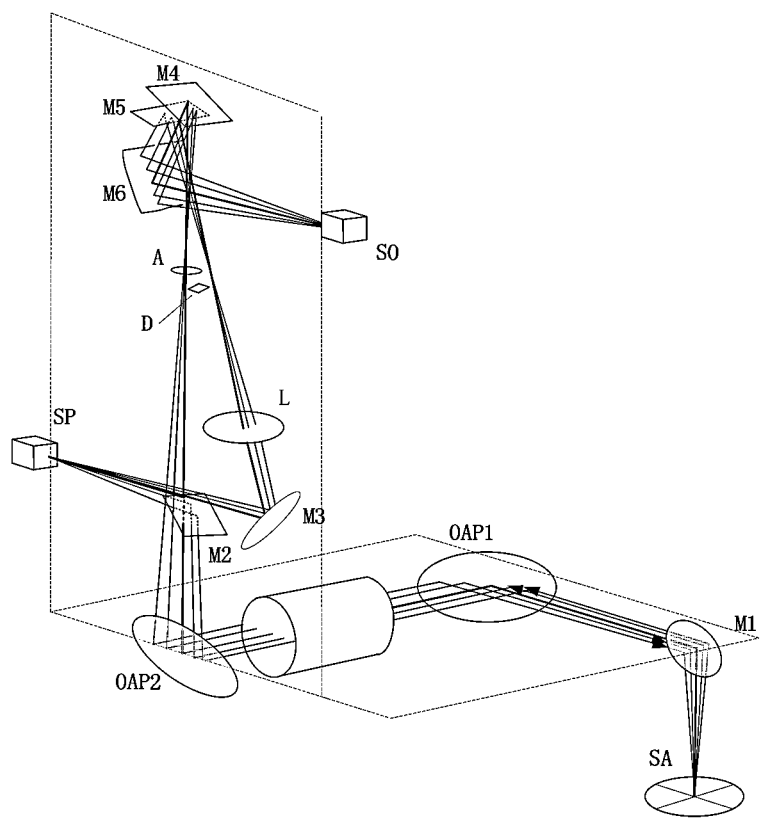
FIG. 17 is a schematic drawing illustrating a normal-incidence broadband spectroscopic polarimeter according to the third embodiment of the invention.

A normal-incidence broadband spectroscopic polarimeter containing reference beam according to the third embodiment of the invention is shown in FIG. 17. The optical path element and measurement method of the embodiment are substantially the same as the first embodiment and the second embodiment. For simplicity, only the optical path of the embodiment is described briefly.

As shown in FIG. 17, the beam emitted from the broadband spot light source SO passes through the curved mirror M6 and is split into two beams by the planar mirrors M5 and M6, one of which is a probing beam, and the other is a reference beam. The probing beam passes through the aperture A, the off-axis parabolic mirror OAP2, and the polarizer P, then is incident on the sample surface perpendicularly after incident on the off-axis parabolic mirror OAP1 and being reflected by the planar mirror M1. The probing beam reflected by the sample surface passes through the off-axis parabolic mirror OAP1, the polarizer P, the off-axis parabolic mirror OAP2 and the planar mirror M2 and is incident on the spectrometer SP. The reference beam passes through the lens L and the planar mirror M3 and is incident on the spectrometer SP. Unlike the first embodiment, the incident surface of the probing beam on the off-axis parabolic mirror OAP1 is perpendicular to the incident surface of the probing beam on the off-axis parabolic mirror OAP2.

Furthermore, the probing beam and the reference beam are within the same plane P1, before the probing beam is emitted from the broadband light source SO to off-axis parabolic mirror OAP2, and before leaving the second off-axis parabolic mirror OAP2 to the broadband spectrometer SP after reflected by sample, and before the reference beam is emitted from the broadband light source SO to the broadband spectrometer SP. The probing beam is within the plane P2 perpendicular to the plane P1 in the optical path between the off-axis parabolic mirror OAP2 and the planar mirror M1.

The embodiment can also add the pattern recognition system as in the first embodiment.

The embodiment can implement the same measurements described in the first embodiment.

Although the first planar mirrors of the first, second and third embodiments can be described as being adjustable or movable, they can also remain fixed. The samples can be placed on a movable or fixed sample stage. In addition, the normal-incidence broadband spectroscopic polarimeter described in the above embodiments also includes an aperture which is located between the polarizer and the sample. The aperture is used for avoiding the e light produced by the polarizer from being incident onto the sample surface and/or the reflected e light from being reflected back to the polarizer. In addition, apertures may be provided in any section of the optical path in the above embodiments. The apertures are perpendicular to the main light and the centre of the apertures passes through the position of the main light to adjust the actual numerical aperture of the probing beam.

Moreover, the normal-incidence broadband spectroscopic polarimeter of the invention can also include a calculating unit, which is used for calculating the optical constants of the sample material and/or analyzing the critical dimension characteristics or three-dimensional profiles of the periodic structure of the sample.

Note that, according to the teaching of the specification, those skilled in the art should understand that, the normal-incidence broadband spectroscopic polarimeter of the invention is not limited to the specific forms disclosed in the above embodiments, the broadband spectrometer can be subjected to all kinds of deformations as long as in accordance with the general concepts of the invention. The broadband spectrometer of the invention can be applied to the measurement of semiconductor thin films, optical masks, metal films, dielectric films, glass (or coating), laser mirrors, thickness and optical constants of organic thin film, and critical dimension and three-dimensional profile of periodic structures consisting of these materials, in particular, can be applied to the measurement of all dimensions of three-dimensional structures with one and two dimensional periodicity and formed by multilayer films and optical constants of layers of material. In addition, the broadband spectrometer of the invention can achieve both auto-focus and manual focus.

Finally, it should be noted that the above embodiments are only to illustrate the technical schemes of the invention and not limiting. While the invention is described in detail with reference to examples, those skilled in the art should understand that modifications or equivalent replacements can occur to the technical schemes of the invention without departing from the spirit and scope of the technical scheme of the invention, all of which should be encompassed within the scope of the claims of the invention.

The invention claimed is:

1. A normal-incidence broadband spectroscopic polarimeter containing reference beam, comprising:
a light source, a first reflecting unit, a first concentrating unit, a second concentrating unit, a polarizer, a first curved mirror, a first planar mirror, a second reflecting unit and a probing unit, wherein
the first reflecting unit is used for splitting light emitted from the light source into a probing beam and a reference beam, and making the probing beam incident on the first concentrating unit, and making the reference beam incident on the second concentrating unit;
the first concentrating unit is used for receiving the probing beam, and making the beam incident on the polarizer after becoming a parallel beam;
the polarizer is provided between the first concentrating unit and the first curved mirror, and used for making the parallel beam pass there through and incident on the first curved mirror;
the first curved mirror is used for receiving the parallel beam passing through the polarizer and making the beam be a focused beam;
the first planar mirror is used for receiving the focused beam and reflecting the focused beam to focus on a sample perpendicularly;
the second concentrating unit is used for receiving the reference beam, and making the reference beam incident on the second reflecting unit;
the second reflecting unit is used for receiving the probing beam reflected by the sample and passing through the planar mirror, the first curved mirror, the polarizer, and the first concentrating unit in order and the reference beam passing through the second concentrating unit respectively or simultaneously, and making the received beams incident on the probing unit; and
the probing unit is used for probing the beam reflected by the second reflecting unit.

2. The normal-incidence broadband spectroscopic polarimeter according to claim 1, wherein the normal-incidence broadband spectroscopic polarimeter also comprises:
a light source concentrating unit, which is provided between the light source and the first reflecting unit, and used for making the light emitted from the light source be focused beam.

3. The normal-incidence broadband spectroscopic polarimeter according to claim 2, wherein the light source concentrating unit comprises:
at least one lens and/or at least one curved mirror.

4. The normal-incidence broadband spectroscopic polarimeter according to claim 1, wherein the normal-incidence broadband spectroscopic polarimeter also comprises:
a moveable beam splitter and a pattern recognition system;
the beam splitter and the pattern recognition system are located between the first curved mirror and the first planar mirror;
the pattern recognition system comprises a lens, an illumination light source and a CCD imager;
the moveable beam splitter is used for reflecting a sample illuminating beam provided by the pattern recognition system to a sample surface and reflecting the reflected beam on the sample surface to the CCD imager; and
in the normal-incidence broadband spectroscopic polarimeter, focusing is adjusted by observing the light intensity of the probing unit and/or by observing the definition of the image in the pattern recognition system.

5. The normal-incidence broadband spectroscopic polarimeter according to claim 4, wherein
the moveable beam splitter is a planar mirror having at least one straight edge, and the planar mirror can be in an optical path fully or partly, or cannot be in the optical path fully.

6. The normal-incidence broadband spectroscopic polarimeter according to claim 1, wherein the normal-incidence broadband spectroscopic polarimeter also comprises:
a beam switching unit for switching the probing beam and the reference beam.

7. The normal-incidence broadband spectroscopic polarimeter according to claim 6, wherein
the beam switching unit is a light blocking plate, which can block the probing beam and the reference beam respectively or simultaneously.

8. The normal-incidence broadband spectroscopic polarimeter according to claim 1, wherein the normal-incidence broadband spectroscopic polarimeter also comprises:
an adjustable sample platform for loading the sample.

9. The normal-incidence broadband spectroscopic polarimeter according to claim 2, wherein the normal-incidence broadband spectroscopic polarimeter also comprises:
an aperture, the aperture being placed in any section of an optical path of the entire optical system.

10. The normal-incidence broadband spectroscopic polarimeter according to claim 9, wherein the normal-incidence broadband spectroscopic polarimeter also comprises:
at least one aperture, the aperture being placed at a focus point of the probing beam split by the focused beam formed by the light source concentrating unit.

11. The normal-incidence broadband spectroscopic polarimeter according to claim 1, wherein the normal-incidence broadband spectroscopic polarimeter also comprises:
at least one aperture, the aperture being located between the polarizer and the sample, and used for avoiding an e light produced after the beam passing through the polarizer from being incident on the sample surface and/or the reflected e light from being reflected back to the polarizer.

12. The normal-incidence broadband spectroscopic polarimeter according to claim 1, wherein the normal-incidence broadband spectroscopic polarimeter also comprises:
a polarizer rotation controlling device, the polarizer rotation controlling device being used for controlling the polarization direction of the polarizer.

13. The normal-incidence broadband spectroscopic polarimeter according to claim 1, wherein the normal-incidence broadband spectroscopic polarimeter also comprises:
a calculating unit, the calculating units being used for calculating optical constants and film thickness of a sample material and/or for analyzing critical dimension characteristics or three-dimensional profile of a periodic structure of the sample.

14. The normal-incidence broadband spectroscopic polarimeter according to claim 1, wherein the first planar mirror and the first curved mirror have the same reflecting material and the same coating structure, and satisfy a condition that the incident angles of the light are the same or approximately the same and incident planes are perpendicular to one another or approximately perpendicular to one another.

15. The normal-incidence broadband spectroscopic polarimeter according to claim 14, wherein
the difference between the incident angle of the main beam of the probing beam on the first planar mirror and the incident angle of the main beam of the probing beam on the first curved mirror does not exceed 5 degrees; and
the incident plane of the incident beam of the first planar mirror is perpendicular to the incident plane of the incident beam of the first curved mirror, and the error of the angle between them is less than 5 degrees.

16. The normal-incidence broadband spectroscopic polarimeter according to claim 1, wherein
the first reflecting unit is composed of at least two planar mirrors, at least one of which has at least one straight edge, the straight edge intersecting with the main light of the optical path.

17. The normal-incidence broadband spectroscopic polarimeter according to claim 1, wherein
the first concentrating unit is an off-axis parabolic mirror or a toroidal mirror.

18. The normal-incidence broadband spectroscopic polarimeter according to claim 1, wherein
the second concentrating unit is a lens, a lens group, an off-axis parabolic mirror or a toroidal mirror.

19. The normal-incidence broadband spectroscopic polarimeter according to claim 1, wherein
the first curved mirror is an off-axis parabolic mirror or a toroidal mirror.

20. The normal-incidence broadband spectroscopic polarimeter according to claim 1, wherein
an inclination angle and/or spatial position of the first planar mirror is adjustable.

21. The normal-incidence broadband spectroscopic polarimeter according to claim 20, wherein
the first planar mirror moves along the propagation direction of the main light of the focused beam.

22. The normal-incidence broadband spectroscopic polarimeter according to claim 1, wherein
the second reflecting unit is composed of at least two planar mirrors, in the planar mirrors constituting the second reflecting unit, at least one having at least one straight edge, the straight edge intersecting with the main light of the optical path.

23. The normal-incidence broadband spectroscopic polarimeter according to claim 1, wherein
the light source is a light source containing multiple wavelengths.

24. The normal-incidence broadband spectroscopic polarimeter according to claim 1, wherein
the light source is a xenon lamp, a deuterium lamp, a tungsten lamp, a halogen lamp, a mercury lamp, a composite broadband light source containing deuterium lamps and tungsten lamps, a composite broadband light source containing tungsten lamps and halogen lamps, a composite broadband light source containing mercury lamps and xenon lamps or a composite broadband light source containing deuterium, tungsten and halogen, or, the light source is a spot light source of natural light with a degree of polarization equal to zero produced by a depolarizer.

25. An optical measurement system, comprising the normal-incidence broadband spectroscopic polarimeter according to claim 1.

* * * * *